under 35 U.S.C. 154(b) by 0 days.

United States Patent
Grecu et al.

(10) Patent No.: US 11,053,223 B2
(45) Date of Patent: Jul. 6, 2021

(54) PHENOXYQUINAZOLINE COMPOUNDS AND THEIR USE IN TREATING CANCER

(71) Applicant: AstraZeneca AB, Södertälje (SE)

(72) Inventors: Tudor Grecu, Cambridge (GB); Jason Grant Kettle, Cambridge (GB); Martin John Packer, Macclesfield (GB); Stuart Eric Pearson, Cambridge (GB); James Michael Smith, Cambridge (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 16/608,212

(22) PCT Filed: Apr. 26, 2018

(86) PCT No.: PCT/EP2018/060800
§ 371 (c)(1),
(2) Date: Oct. 25, 2019

(87) PCT Pub. No.: WO2018/197643
PCT Pub. Date: Nov. 1, 2018

(65) Prior Publication Data
US 2020/0223828 A1 Jul. 16, 2020

Related U.S. Application Data

(60) Provisional application No. 62/490,865, filed on Apr. 27, 2017.

(51) Int. Cl.
| | |
|---|---|
| *C07D 403/12* | (2006.01) |
| *A61K 31/517* | (2006.01) |
| *A61P 35/00* | (2006.01) |
| *A61P 35/04* | (2006.01) |
| *C07D 405/14* | (2006.01) |

(52) U.S. Cl.
CPC ............ *C07D 403/12* (2013.01); *A61P 35/04* (2018.01); *C07D 405/14* (2013.01); *C07B 2200/13* (2013.01)

(58) Field of Classification Search
CPC ...... C07D 403/12; A61K 31/517; A61P 35/00
See application file for complete search history.

(56) References Cited

U.S. PATENT DOCUMENTS

2003/0087907 A1   5/2003   Kubo et al.

FOREIGN PATENT DOCUMENTS

WO   WO-2006/040520 A1   4/2006

OTHER PUBLICATIONS

Antonescu et al., Acquired Resistance to Imatinib in Gastrointestinal Stromal Tumor Occurs Through Secondary Gene Mutation, Clin. Cancer Res., 11(11):4182-90 (2005).

Babaei et al., Receptor tyrosine kinase (c-Kit) inhibitors: a potential therapeutic target in cancer cells, Drug Design, Development and Therapy, vol. 10, pp. 2443-2459 (Aug. 2016).
Bahlawane et al., Constitutive Activation of Oncogenic PDGFRa-mutant Proteins Occurring in GIST Patients Induces Receptor Mislocalisation and Alters PDGFRa Signalling Characteristics, Cell Commun. Signal, 13:21 (2015).
Barnett et al., Gastrointestinal Stromal Tumors: Molecular Markers and Genetic Subtypes, Hematol. Oncol. Clin. North Am., 27(5):871-88 (2013).
Blanke et al., Phase III Randomized, Intergroup Trial Assessing Imatinib Mesylate at Two Dose Levels in Patients With Unresectable or Metastatic Gastrointestinal Stromal Tumors Expressing the Kit Receptor Tyrosine Kinase: S0033, J. Clin. Oncol., 26(4):626-32 (2008).
Demetri et al., Efficacy and Safety of Imatinib Mesylate in Advanced Gastrointestinal Stromal Tumors, N Engl J Med., 347(7):472-80 (2002).
Demetri et al., Efficacy and Safety of Regorafenib for Advanced Gastrointestinal Stromal Tumours After Failure of Imatinib and Sunitinib (GRID): An International, Multicentre, Randomised, Placebo-Controlled, Phase 3 Trial, Lancet, 381(9863):295-302 (2013).
Demetri et al., Efficacy and Safety of Sunitinib in Patients With Advanced Gastrointestinal Stromal Tumour After Failure of Imatinib: A Randomised Controlled Trial, Lancet, 368(9544):1329-38 (2006).
DiNitto et al., Function of Activation Loop Tyrosine Phosphorylation in the Mechanism of c-Kit Auto-Activation and Its Implication in Sunitinib Resistance, J. Biol. Chem., 147(4):601-9 (2010).
Fletcher, Kit Oncogenic Mutations: Biologic Insights, Therapeutic Advances, and Future Directions, Cancer Res., 76(21):6140-2 (2016).
Gastrointestinal Stromal Tumor Meta-Analysis Group (MetaGIST), Comparison of Two Doses of Imatinib for the Treatment of Unresectable or Metastatic Gastrointestinal Stromal Tumors: A Meta-Analysis of 1,640 Patients, J. Clin. Oncol., 28(7):1247-53 (2010).

(Continued)

*Primary Examiner* — Bruck Kifle
(74) *Attorney, Agent, or Firm* — Marshall, Gerstein & Borun LLP

(57) ABSTRACT

The invention concerns compounds of Formula (I): or pharmaceutically acceptable salts thereof, wherein $R^1$, $R^2$, $R^3$ and $R^4$ have any of the meanings hereinbefore defined in the description; process for their preparation, pharmaceutical compositions containing them and their use in treating KIT mediated diseases.

(I)

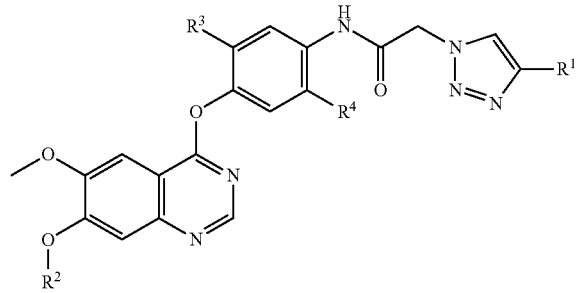

10 Claims, 4 Drawing Sheets

(56) References Cited

OTHER PUBLICATIONS

Heinrich et al., Molecular Correlates of Imatinib Resistance in Gastrointestinal Stromal Tumors, J. Clin. Oncol., 24(29):4764-74 (2006).
Heinrich et al., Primary and Secondary Kinase Genotypes Correlate With the Biological and Clinical Activity of Sunitinib in Imatinib-Resistant Gastrointestinal Stromal Tumor, J. Clin. Oncol., 26(33):5352-9 (2008).
Hirota et al., Gain-of-function Mutations of C-Kit in Human Gastrointestinal Stromal Tumors, Science, 279(5350):577-80 (1998).
International Application No. PCT/EP2018/060800, International Search Report and Written Opinion, dated Jul. 6, 2018.
Lemmon et al., A New Twist in the Transmembrane Signaling Tool-Kit, Cell, 130(2):213-5 (2007).
Lennartsson et al., Stem Cell Factor receptor/c-Kit: From Basic Science to Clinical Implications, Physiol. Rev., 92(4):1619-49 (2012).
Ple et al., Discovery of AZD2932, a New Quinazoline Ether Inhibitor With High Affinity for VEGFR-2 and PDGFR Tyrosine Kinases, Bioorg. Med. Chem. Lett., 22(1):262-6 (2012).
Verstraete et al., Extracellular Assembly and Activation Principles of Oncogenic Class III Receptor Tyrosine Kinases, Nat Rev Cancer, 12(11):753-66 (2012).
Verweij et al., Progression-free Survival in Gastrointestinal Stromal Tumours With High-Dose Imatinib: Randomised Trial, Lancet, 364(9440):1127-34 (2004).
Babaei, M. et al.; "Receptor tyrosine kinase (c-Kit) inhibitors: a potential therapeutic target in cancer cells;" *Drug Design, Development and Therapy*; 2016:10 (pp. 2443-2459).
Denisko, O. et al.; "Heterocyclic compound;" Britannica; https://www.britannica.com/science/heterocyclic-compound; printed Dec. 17, 2020 (pp. 1-7).
Heinrich, M. et al. "Inhibition of KIT Tyrosine Kinase Activity: A Novel Molecular Approach to the Treatment of KIT-Positive Malignancies;" Journal of Clinical Oncology, vol. 20, No. 6 (Mar. 15, 2002); (pp. 1692-1703).
IUPAC; "Compendium of Chemical Terminology Gold Book;" Compendium of Chemical Terminology; Version 2.3.3; Feb. 24, 2014 (p. 673).

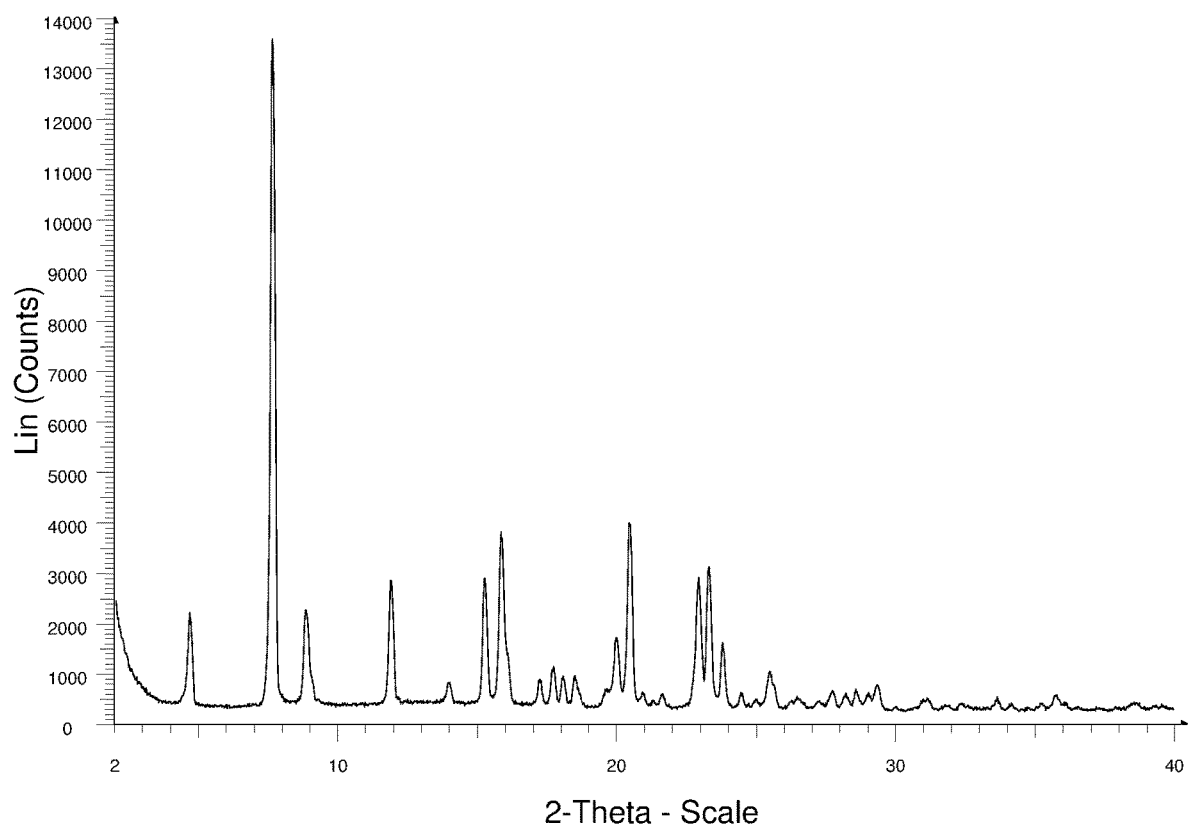
FIG. 1: XRPD Compound A, Form A

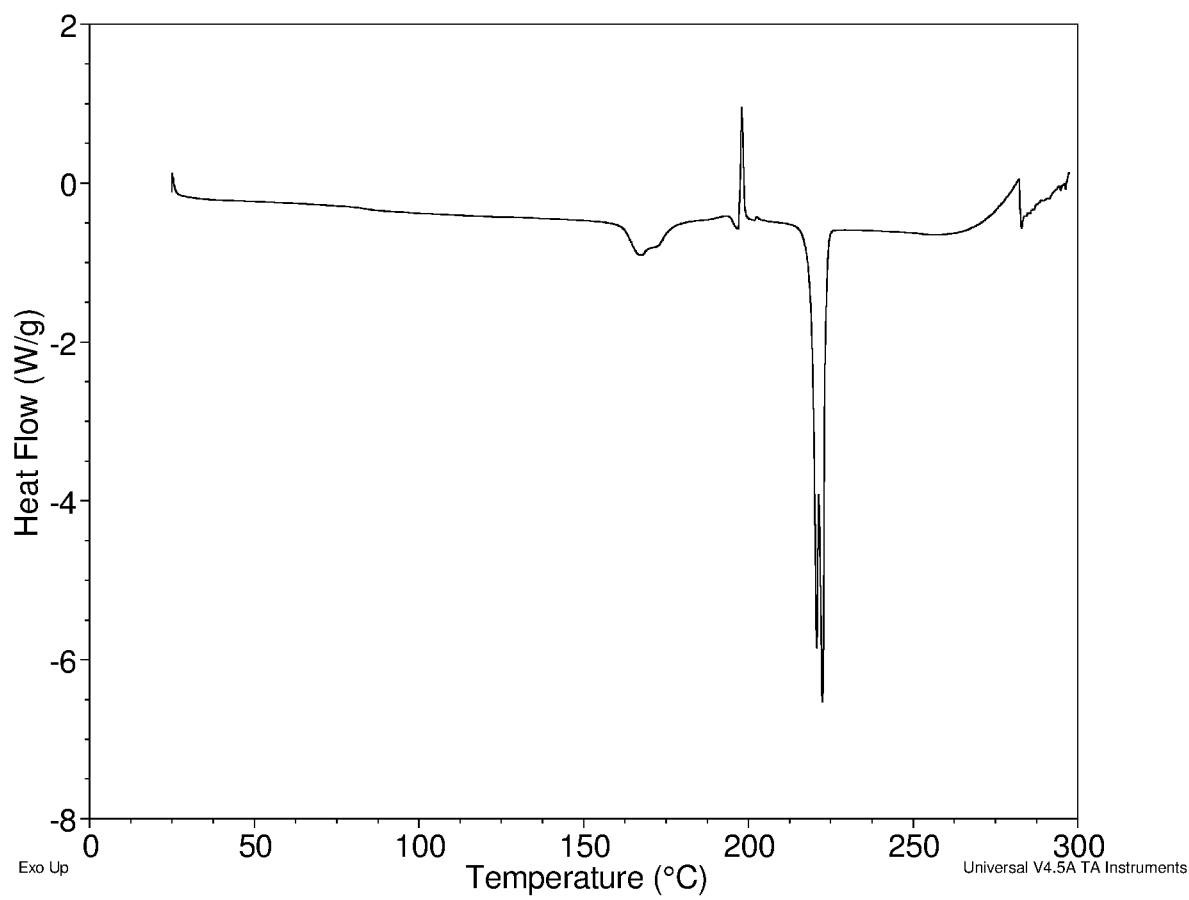
FIG. 2: DSC thermogram of Compound A, Form A

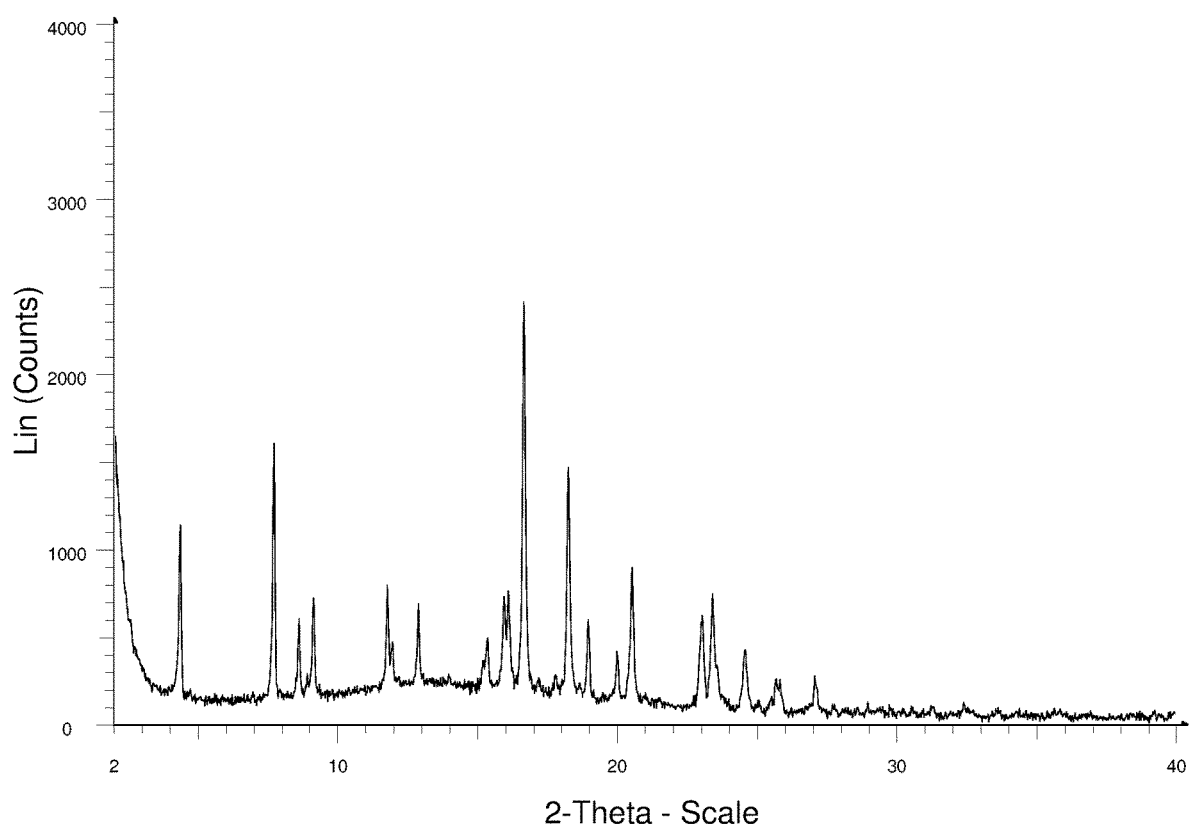
FIG. 3: XRPD Compound A, Form B

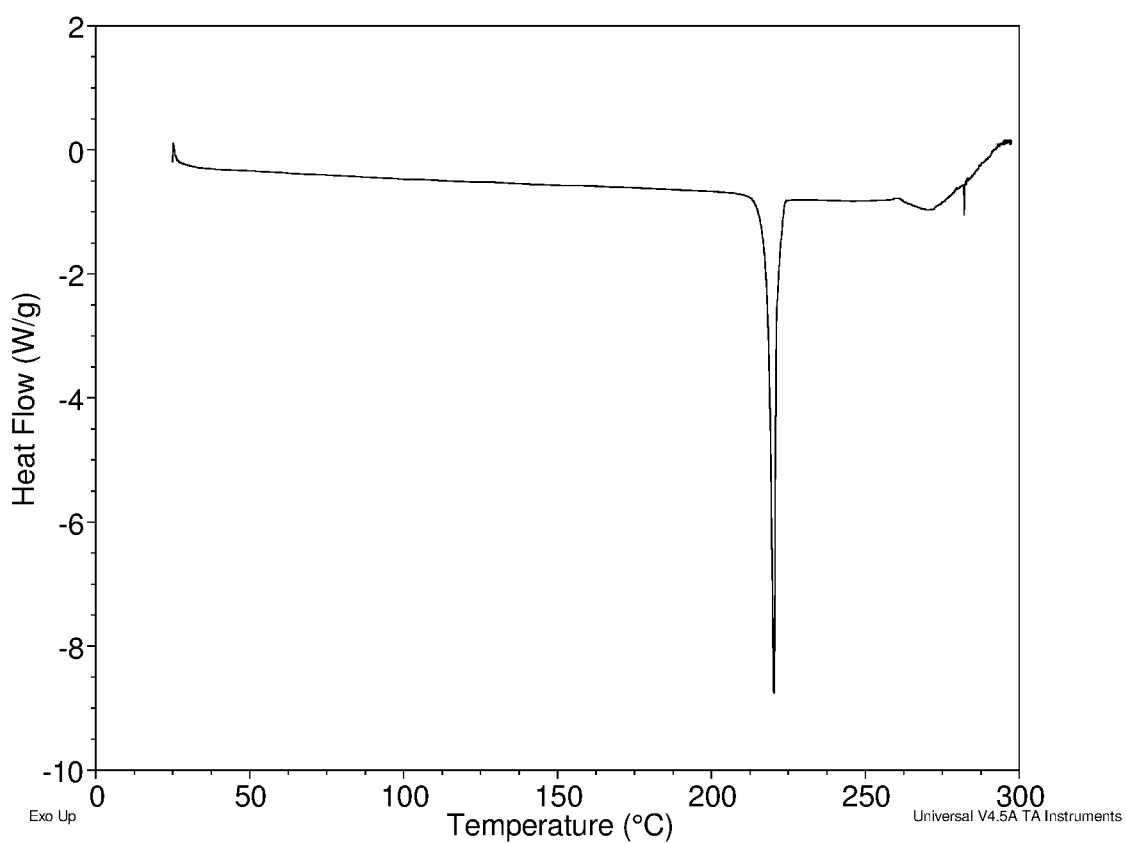
FIG. 4: DSC thermogram of Compound A, Form B

PHENOXYQUINAZOLINE COMPOUNDS AND THEIR USE IN TREATING CANCER

FIELD OF INVENTION

The specification generally relates to substituted phenoxyquinazoline compounds and pharmaceutically acceptable salts thereof. These compounds and their pharmaceutically acceptable salts selectively modulate KIT, including wildtype KIT and primary and secondary KIT mutations, and the specification therefore also relates to the use of such compounds and salts thereof to treat or prevent KIT mediated disease, including cancer. The specification further relates to crystalline forms of substituted phenoxyquinazoline compounds and pharmaceutically acceptable salts thereof; pharmaceutical compositions comprising such compounds and salts; kits comprising such compounds and salts; methods of manufacture of such compounds and salts; and to methods of treating KIT mediated disease, including cancer, using such compounds and salts.

BACKGROUND

Receptor tyrosine kinases (RTK) can be oncogenic drivers in cancer due to genetic aberrations such as amplification, mutations or fusion events or via overexpression (M. A. Lemmon, K. M. Ferguson, Cell 130, 213 (2007)). Most aberrations in RTK result in ligand-independent activation of the receptor and activation of downstream signalling promoting cell growth and proliferation and increased survival. The class III RTK including KIT, platelet-derived growth factor receptor (PDGFR) alpha and beta, colony-stimulating factor 1 receptor (CSF1R), and the Fms-like tyrosine kinase 3 receptor (FLT3) is implicated in a variety of human cancers (K. Verstraete, S. N. Savvides, Nat. Rev. Cancer 12, 753 (2012)).

The gene encoding KIT is located on Chr 4 and comprises 21 exons (J. Lennartsson, L. Ronnstrand, Physiol Rev. 92, 1619 (2012)). The 976 amino acids of the KIT protein are divided into key domains: an extracellular domain, a transmembrane domain, a juxtamembrane domain (JM) and kinase domain separated by a kinase insert (KID) in the middle. The mature protein is ~145 KDa following N glycosylation and is expressed at the cell surface. Following stem cell factor (SCF) binding, the dimerisation increases the intrinsic kinase activity phosphorylating tyrosine residues in the JM domain (Y547, Y553, Y568 and Y570) followed by phosphorylations in the KID (Y703, Y721, Y729/730) and finally the activation loop (Y823) (J. P. DiNitto et al., J. Biochem. 147, 601 (2010)). Some phosphoylations sites on KIT are key docking sites for adaptors and downstream effectors propagating the activation signal. PI3K, Src and MAPK are key signalling pathways activated downstream of KIT. Regulation of KIT signalling includes internalization and subsequent degradation of the receptor, phosphorylation of Ser 741 and 746, and dephosphorylation of tyrosine residues by phosphatases such as SHP1.

KIT-driven signaling plays a key role in specific cell types, including interstitial cells of Cajal (ICCs), melanocytes, mast cells, germ cells and some hematopoietic stem cells (J. Lennartsson, L. Ronnstrand, Physiol Rev. 92, 1619 (2012)). Aberrations of KIT are observed in malignancies derived from these cell types. For example, KIT mutations are reported in gastrointestinal stromal tumours (originating from ICC), in mastocytosis and in melanomas.

Mutations in KIT in cancer affect multiple exons with hotspot mutations observed in the JM and kinase domains (J. Lennartsson, L. Ronnstrand, Physiol Rev. 92, 1619 (2012)). Mutations in the JM domain are thought to remove the autoinhibitory interaction of the JM domain with the kinase domain (J. P. DiNitto et al., J. Biochem. 147, 601 (2010)). Lower frequency mutations are present in exon 9 (extracellular Ig domain 5) and 13 (ATP binding pocket and gatekeeper). Mutations in the JM domain are observed in GIST while mutations affecting the kinase domain, in particular the A loop are frequently observed in mastocytosis. Similarly, PDGFR mutations in GIST affect both the JM domain and the kinase domain (C. Bahlawane et al., Cell Commun. Signal. 13, 21 (2015)).

Gastrointestinal stromal tumors (GISTs) are the most common mesenchymal tumors of the gastrointestinal tract (C. M. Barnett, C. L. Corless, M. C. Heinrich, Hematol. Oncol. Clin. North Am. 27, 871 (2013)). GISTs are most commonly found in the stomach and small intestine. Neoplastic GIST originate from the same precursor cells as the ICC and the vast majority of GIST express KIT protein initially called CD117. KIT mutations affecting exon 11 were first identified in GIST in 1998 (S. Hirota et al., Science 279, 577 (1998)). The same publication also reported the oncogenicity of KIT mutations expressed ectopically in Ba/F3 cells and their constitutive kinase activation. 75-80% GIST harbor KIT mutations and ~10% PDGFR mutations (J. A. Fletcher, Cancer Res. 76, 6140 (2016)). Rare aberrations in BRAF, NF1 and SDH account for what is referred to as WT KIT (C. M. Barnett, C. L. Corless, M. C. Heinrich, Hematol. Oncol. Clin. North Am. 27, 871 (2013)).

Imatinib was the first KIT inhibitor tested in GIST, demonstrating remarkable activity in patients with advanced GIST (G. D. Demetri et al., N. Engl. J. Med. 347, 472 (2002), J. Verweij et al., Lancet 364, 1127 (2004), C. D. Blanke et al., J. Clin. Oncol. 26, 626 (2008)). A meta-analysis of 2 large clinical studies concluded that patients with exon 9 mutations in KIT or other mutations had worse prognosis than patients with exon 11 mutations (Metagist, J. Clin. Oncol. 28, 1247 (2010)). In addition, a high dose imatinib (800 mg) did not improve progression-free survival in patients with exon 9 mutations compared to the standard dose (400 mg). Clinical resistance to imatinib was first reported in 2005 (C. R. Antonescu et al., Clin. Cancer Res. 11, 4182 (2005)) but a larger study following patients treated with imatinib as part of a PhII study B2222 showed a reactivation of KIT and KIT signalling when patients who have initially benefited from imatinib relapsed (M. C. Heinrich et al., J. Clin. Oncol. 24, 4764 (2006)). Secondary resistance mutations were noted at key residues: V654A in the ATP-binding pocket, T670I at the gatekeeper residue and A loop (D816X, D820X, N822K, Y823D). In addition, so called "primary resistance" to imatinib was mainly observed in patients with exon9 mutations. Overall, 50% of patients developed resistance within 2 years (C. D. Blanke et al., J. Clin. Oncol. 26, 626 (2008).).

Sunitinib is a multikinase inhibitor including KIT and PDGFR. Sunitinib demonstrated clinical activity in GIST patients following progression on imatinib (G. D. Demetri et al., Lancet 368, 1329 (2006)). Clinical benefit with sunitinib was observed in patients with primary exon 9 mutations. In addition, patients with secondary mutations affecting exon 13 and 14 had longer progression-free and overall survival compared to patients with secondary mutations affecting the A loop (M. C. Heinrich et al., J. Clin. Oncol. 26, 5352 (2008)). Clinical progression with sunitnib was observed within 1 year of treatment. Ectopic expression of KIT with primary and secondary mutations in CHO cells showed that sunitinib reduced KIT phosphorylation preferentially when KIT aberrations affected the ATP binding pocket or the gatekeeper.

Regorafenib, another multikinase inhibitor has shown clinical activity in patients with GIST after relapse to imatinib and sunitinib (G. D. Demetri et al., *Lancet* 381, 295 (2013)). The PhIII study reported a median PFS of 4.8 months.

Accordingly, there is a need for KIT inhibitors that inhibit secondary KIT mutations, and furthermore, are selective against KDR, particularly as existing treatments are ineffective against such secondary mutations. There is also a need for KIT inhibitors that inhibit primary KIT mutations and wildtype KIT.

SUMMARY

The compounds of the disclosure have been found to possess potent anti-tumour activity, being useful in inhibiting a range of secondary KIT mutations, including V654A, D816H and T670I, as well as primary mutations and wildtype KIT, and furthermore are selective against KDR. The compounds of the disclosure have the required pharmaceutical properties, for example, good PK properties.

Briefly, this specification describes in part, a compound of Formula (I)

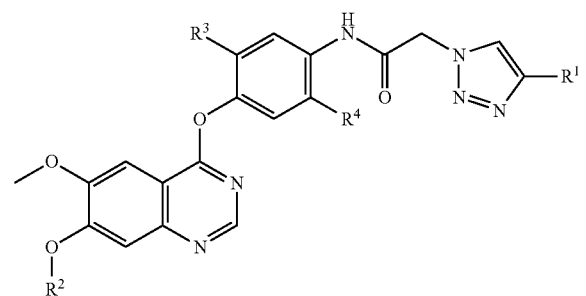

or a pharmaceutically acceptable salt thereof, wherein:
$R^1$ is a $C_{2-3}$ alkyl or a cyclopropyl group;
$R^2$ is a $C_{1-3}$ alkyl, optionally substituted with a group selected from hydroxyl, $C_{1-3}$ alkoxy and —$NR^5R^6$, where $R^5$ and $R^6$ are each independently hydrogen or methyl or $R^5$ and $R^6$ together with the nitrogen to which they are attached form a 5 membered heterocyclyl ring; or a 4 to 6 membered heterocyclyl containing one oxygen atom;
$R^3$ is hydrogen or fluoro; and
$R^4$ is hydrogen or methoxy.

This specification also describes, in part, a pharmaceutical composition which comprises a compound of Formula (I), or a pharmaceutically acceptable salt thereof, and at least one pharmaceutically acceptable diluent or carrier.

This specification also describes, in part, a compound of Formula (I), or a pharmaceutically acceptable salt thereof, for use in therapy.

This specification also describes, in part, a compound of Formula (I), or a pharmaceutically acceptable salt thereof, for use in the treatment of cancer.

This specification also describes, in part, a compound of Formula (I), or a pharmaceutically acceptable salt thereof, for the manufacture of a medicament for the treatment of cancer.

This specification also describes, in part, a method for treating cancer in a warm blooded animal in need of such treatment, which comprises administering to the warm-blooded animal a therapeutically effective amount of a compound of Formula (I), or a pharmaceutically acceptable salt thereof.

BRIEF DESCRIPTION OF THE FIGURES

FIG. 1 shows the XRPD for Form A of N-(4-((6,7-Dimethoxyquinazolin-4-yl)oxy)phenyl)-2-(4-isopropyl-1H-1,2,3-triazol-1-yl)acetamide (Compound A, Example 1).

FIG. 2 shows the DSC for Form A of N-(4-((6,7-Dimethoxyquinazolin-4-yl)oxy)phenyl)-2-(4-isopropyl-1H-1,2,3-triazol-1-yl)acetamide (Compound A, Example 1).

FIG. 3 shows the XRPD for Form B of N-(4-((6,7-Dimethoxyquinazolin-4-yl)oxy)phenyl)-2-(4-isopropyl-1H-1,2,3-triazol-1-yl)acetamide (Compound A, Example 1).

FIG. 4 shows the DSC for Form B of N-(4-((6,7-Dimethoxyquinazolin-4-yl)oxy)phenyl)-2-(4-isopropyl-1H-1,2,3-triazol-1-yl)acetamide (Compound A, Example 1).

DESCRIPTION OF ILLUSTRATIVE EMBODIMENTS

Many embodiments of the invention are detailed throughout the specification and will be apparent to a reader skilled in the art. The invention is not to be interpreted as being limited to any particular embodiment(s) thereof.

In the first embodiment there is provided a compound of Formula (I):

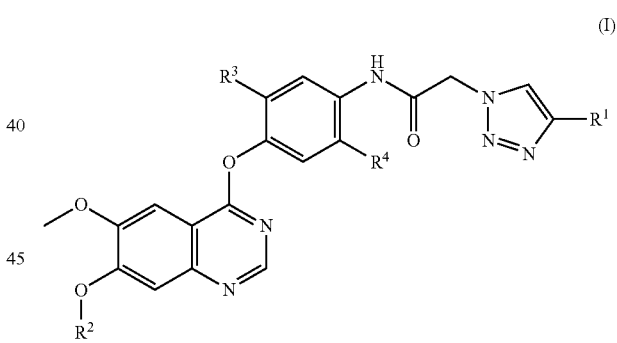

or a pharmaceutically acceptable salt thereof, wherein:
$R^1$ is a $C_{2-3}$ alkyl or a cyclopropyl group;
$R^2$ is a $C_{1-3}$ alkyl, optionally substituted with a group selected from hydroxyl, $C_1$-$C_3$ alkoxy, or —$NR^5R^6$, where $R^5$ and $R^6$ are each independently hydrogen or methyl or $R^5$ and $R^6$ together with the nitrogen to which they are attached form a 5 membered heterocyclyl ring; or a 4 to 6 membered heterocyclyl containing one oxygen atom;
$R^3$ is hydrogen or fluoro; and
$R^4$ is hydrogen or methoxy.

Suitable 4 to 6 membered heterocyclyl rings containing one oxygen atom include an oxetanyl ring, a tetrahydrofuranyl ring and an oxanyl ring.

The term "oxetanyl" ring includes oxetan-3-yl, the structure of which is shown below

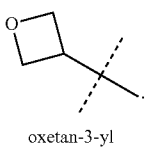

oxetan-3-yl

The term "tetrahydrofuranyl" includes tetrahydrofuran-3-yl, the structure of which is shown below.

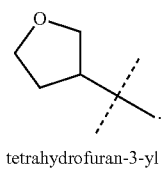

tetrahydrofuran-3-yl

The term "oxanyl ring" includes oxan-3-yl and oxan-4-yl groups, the structures of which are shown below.

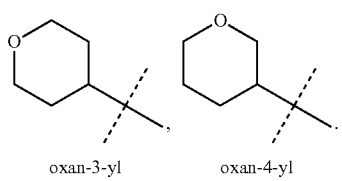

oxan-3-yl        oxan-4-yl

In the above structures the dashed line indicates the bonding position of the relevant group.

An oxanyl ring may also be referred to as a tetrahydropyranyl ring. Similarly, an oxan-4-yl ring may be referred to as a tetrahydropyran-4-yl ring, and an oxan-3-yl ring may be referred to as a tetrahydropyran-3-yl ring.

The prefix $C_{p-q}$ in $C_{p-q}$ alkyl and other terms (where p and q are integers) indicates the range of carbon atoms that are present in the group, for example $C_{1-3}$ alkyl includes $C_1$ alkyl (methyl), $C_2$ alkyl (ethyl) and $C_3$ alkyl (propyl as n-propyl and isopropyl).

The term $C_{p-q}$ alkoxy comprises —O—$C_{p-q}$ alkyl groups.

Where the term "optionally" is used, it is intended that the subsequent feature may or may not occur. As such, use of the term "optionally" includes instances where the feature is present, and also instances where the feature is not present. For example, a group "optionally substituted by one methoxy group" includes groups with and without a methoxy substituent.

The term "substituted" means that one or more hydrogens (for example one or two hydrogens, or alternatively one hydrogen) on the designated group is replaced by the indicated substituent(s) (for example one or two substituents, or alternatively one substituent), provided that any atom(s) bearing a substituent maintains a permitted valency. Substituent combinations encompass only stable compounds and stable synthetic intermediates. "Stable" means that the relevant compound or intermediate is sufficiently robust to be isolated and have utility either as a synthetic intermediate or as an agent having potential therapeutic utility. If a group is not described as "substituted", or "optionally substituted", it is to be regarded as unsubstituted (i.e. that none of the hydrogens on the designated group have been replaced).

The term "pharmaceutically acceptable" is used to specify that an object (for example a salt, dosage form, diluent or carrier) is suitable for use in patients. An example list of pharmaceutically acceptable salts can be found in the *Handbook of Pharmaceutical Salts: Properties, Selection and Use*, P. H. Stahl and C. G. Wermuth, editors, Weinheim/Zürich:Wiley-VCH/VHCA, 2002. A suitable pharmaceutically acceptable salt of a compound of Formula (I) is, for example, an acid addition salt. An acid addition salt of a compound of Formula (I) may be formed by bringing the compound into contact with a suitable inorganic or organic acid under conditions known to the skilled person. An acid addition salt may for example be formed using an inorganic acid selected from the group consisting of hydrochloric acid, hydrobromic acid, sulphuric acid and phosphoric acid. An acid addition salt may also be formed using an organic acid selected from the group consisting of trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid and para-toluenesulfonic acid.

A further embodiment provides any of the embodiments defined herein (for example the embodiment of claim 1) with the proviso that one or more specific Examples (for instance, one, two or three specific Examples) selected from the group consisting of Examples 1, 2, 3, 4, 5, 6, 7, 8, 9, 10, 11, 12 and 13 is individually disclaimed.

In one embodiment, $R^1$ is selected from ethyl, isopropyl and cyclopropyl. In one embodiment $R^1$ is ethyl. In one embodiment $R^1$ is isopropyl. In one embodiment $R^1$ is cyclopropyl.

In one embodiment $R^2$ is selected from $C_{1-3}$ alkyl optionally substituted with a group selected from hydroxyl, methoxyl, —$NR^5R^6$ where $R^5$ and $R^6$ are each independently hydrogen or methyl, or $R^5$ and $R^6$ together with the nitrogen to which they are attached form a 5 membered heterocyclyl ring; and an oxetanyl, a tetrahydrofuranyl and an oxanyl ring.

In one embodiment $R^2$ is selected from methyl, isopropyl, hydroxyethyl, 2-(dimethylamino)ethyl, 2-(pyrrolidin-1-yl) ethyl), 2-methoxyethyl, oxetan-3-yl, tetrahydrofuran-3-yl and oxan-4-yl.

In one embodiment $R^2$ is methyl. In one embodiment $R^2$ is isopropyl. In one embodiment $R^2$ is hydroxyethyl. In one embodiment $R^2$ is 2-(dimethylamino)ethyl. In one embodiment $R^2$ is 2-(pyrrolidin-1-yl)ethyl). In one embodiment $R^2$ is 2-methoxyethyl. In one embodiment $R^2$ is oxetan-3-yl. In one embodiment $R^2$ is tetrahydrofuran-3-yl. In one embodiment $R^2$ is oxan-4-yl.

In one embodiment $R^3$ is hydrogen. In one embodiment $R^3$ is fluoro.

In one embodiment $R^4$ is hydrogen. In one embodiment $R^4$ is methoxy.

In one embodiment $R^1$ is isopropyl, $R^2$ is methyl and $R^3$ and $R^4$ are both independently hydrogen.

In one embodiment there is provided a compound of Formula (I), or a pharmaceutically acceptable salt thereof, wherein the compound is selected from the group consisting of:

N-(4-((6,7-Dimethoxyquinazolin-4-yl)oxy)phenyl)-2-(4-isopropyl-1H-1,2,3-triazol-1-yl)acetamide;

2-(4-Cyclopropyl-1H-1,2,3-triazol-1-yl)-N-(4-((6,7-dimethoxyquinazolin-4-yl)oxy)phenyl)acetamide;

N-(4-((6,7-Dimethoxyquinazolin-4-yl)oxy)-2-methoxyphenyl)-2-(4-isopropyl-1H-1,2,3-triazol-1-yl)acetamide;

N-(4-((6,7-Dimethoxyquinazolin-4-yl)oxy)-3-fluorophenyl)-2-(4-isopropyl-1H-1,2,3-triazol-1-yl)acetamide;

2-(4-Isopropyl-1H-1,2,3-triazol-1-yl)-N-(4-((6-methoxy-7-(2-methoxyethoxy)quinazolin-4-yl)oxy)phenyl)acetamide;

2-(4-Isopropyl-1H-1,2,3-triazol-1-yl)-N-(4-((6-methoxy-7-(2-(pyrrolidin-1-yl)ethoxy)quinazolin-4-yl)oxy)phenyl)acetamide N-(4-((7-(2-(Dimethylamino)ethoxy)-6-methoxyquinazolin-4-yl)oxy)phenyl)-2-(4-isopropyl-1H-1,2,3-triazol-1-yl)acetamide;

N-(4-((7-(2-Hydroxyethoxy)-6-methoxyquinazolin-4-yl)oxy)phenyl)-2-(4-isopropyl-1H-1,2,3-triazol-1-yl)acetamide;

2-(4-Isopropyl-1H-1,2,3-triazol-1-yl)-N-(4-((6-methoxy-7-((tetrahydro-2H-pyran-4-yl)oxy)quinazolin-4-yl)oxy)phenyl)acetamide;

2-(4-Isopropyl-1H-1,2,3-triazol-1-yl)-N-(4-((6-methoxy-7-(oxetan-3-yloxy)quinazolin-4-yl)oxy)phenyl)acetamide;

N-[4-(7-Isopropoxy-6-methoxy-quinazolin-4-yl)oxyphenyl]-2-(4-isopropyl-1H-1,2,3-triazol-1-yl)acetamide;

(R)-2-(4-Isopropyl-1H-1,2,3-triazol-1-yl)-N-(4-((6-methoxy-7-((tetrahydrofuran-3-yl)oxy)quinazolin-4-yl)oxy)phenyl)acetamide; and (S)-2-(4-Isopropyl-1H-1,2,3-triazol-1-yl)-N-(4-((6-methoxy-7-((tetrahydrofuran-3-yl)oxy)quinazolin-4-yl)oxy)phenyl)acetamide.

In one embodiment there is provided a compound of Formula (I), or a pharmaceutically acceptable salt thereof, wherein the compound is N-(4-((6,7-Dimethoxyquinazolin-4-yl)oxy)phenyl)-2-(4-isopropyl-1H-1,2,3-triazol-1-yl)acetamide (also referred to as Compound A).

Compounds and salts described in this specification may exist in solvated forms and unsolvated forms. For example, a solvated form may be a hydrated form, such as a hemihydrate, a mono-hydrate, a di-hydrate, a tri-hydrate or an alternative quantity thereof. The invention encompasses all such solvated and unsolvated forms of compounds of Formula (I), particularly to the extent that such forms possess KIT inhibitory activity, as for example measured using the tests described herein.

Atoms of the compounds and salts described in this specification may exist as their isotopes. The invention encompasses all compounds of Formula (I) where an atom is replaced by one or more of its isotopes (for example a compound of Formula (I) where one or more carbon atom is an $^{11}C$ or $^{13}C$ carbon isotope, or where one or more hydrogen atoms is a $^{2}H$ or $^{3}H$ isotope, or where one or more nitrogen atoms is a $^{15}N$ isotope or where one of more oxygen atoms is an $^{17}O$ or $^{18}O$ isotope).

Compounds and salts described in this specification may exist in optically active or racemic forms by virtue of one or more asymmetric carbon atoms. The invention includes any optically active or racemic form of a compound of Formula (I) which possesses KIT inhibitory activity, as for example measured using the tests described herein. The synthesis of optically active forms may be carried out by standard techniques of organic chemistry well known in the art, for example by synthesis using optically active materials or by resolution of a racemic form.

Therefore, in one embodiment there is provided a compound of Formula (I), or a pharmaceutically acceptable salt thereof, which is a single optical isomer being in an enantiomeric excess (% e.e.) of ≥95%, ≥98% or ≥99%. In one embodiment, the single optical isomer is present in an enantiomeric excess (% e.e.) of ≥99%.

Some of the compounds of Formula (I) may be crystalline and may have more than one crystalline form. It is to be understood that the invention encompasses any crystalline or amorphous form, or mixtures thereof, which form possess properties useful in KIT inhibitory activity. It is well known how to determine the efficacy of a crystalline or amorphous form by the standard tests described hereinafter.

It is generally known that crystalline materials may be analysed using conventional techniques such as, for example, X-ray powder diffraction (hereinafter XRPD) analysis and Differential Scanning Calorimetry (hereinafter DSC).

As an example, the compound of Example 1 exhibits crystallinity and two crystalline forms, Form A and Form B, have been identified.

Accordingly, a further aspect of the invention is Form A of Compound A (Example 1).

According to the invention, there is provided a crystalline form, Form A, of Compound A which has an XRPD pattern with at least one specific peak at about 2-theta=4.7°, measured using CuKα radiation.

According to the invention there is provided a crystalline form, Form A, of Compound A which has an XRPD pattern with at least one specific peak at about 2-theta=8.9°, measured using CuKα radiation.

According to the invention there is provided a crystalline form, Form A, of Compound A which has an XRPD pattern with at least two specific peaks at about 2-theta=4.7° and 8.9°, measured using CuKα radiation.

According to the invention there is provided a crystalline form, Form A, of Compound A which has an XRPD pattern with specific peaks at about 2-theta=4.7, 7.6, 8.9, 11.9, 15.3, 15.9, 20.0, 20.5, 22.9 and 23.3°, measured using CuKα radiation.

According to the invention there is provided a crystalline form, Form A, of Compound A which has an XRPD pattern substantially the same as the XRPD shown in FIG. 1, measured using CuKα radiation.

According to a further aspect of the invention, there is provided a crystalline form, Form A, of Compound A which has an XRPD pattern with at least one specific peak at 2-theta=4.7° plus or minus 0.2° 2-theta, measured using CuKα radiation.

According to the invention there is provided a crystalline form, Form A, of Compound A which has an XRPD pattern with at least one specific peak at 2-theta=8.9° plus or minus 0.2° 2-theta, measured using CuKα radiation.

According to the invention there is provided a crystalline form, Form A, of Compound A which has an XRPD pattern with at least two specific peaks at 2-theta=4.7° and 8.9° plus or minus 0.2° 2-theta, measured using CuKα radiation.

According to the invention there is provided a crystalline form, Form A, of Compound A which has an XRPD pattern with specific peaks at 2-theta=4.7, 7.6, 8.9, 11.9, 15.3, 15.9, 20.0, 20.5, 22.9 and 23.3° plus or minus 0.2° 2-theta, measured using CuKα radiation.

The DSC analysis of Form A of Compound A is shown in FIG. 2.

Accordingly, a further aspect of the invention is Form B of Compound A.

According to the invention, there is provided a crystalline form, Form B, of Compound A which has an XRPD pattern with at least one specific peak at about 2-theta=4.3°, measured using CuKα radiation.

According to the invention there is provided a crystalline form, Form B, of Compound A which has an XRPD pattern with at least one specific peak at about 2-theta=16.6°, measured using CuKα radiation.

According to the invention there is provided a crystalline form, Form B, of Compound A which has an XRPD pattern with at least two specific peaks at about 2-theta=4.3° and 16.6°, measured using CuKα radiation.

According to the invention there is provided a crystalline form, Form B, of Compound A which has an XRPD pattern with specific peaks at about 2-theta=4.3, 7.7, 9.1, 11.8, 12.8, 15.9, 16.6, 18.2, 20.5, 23.4°, measured using CuKα radiation.

According to the invention there is provided a crystalline form, Form B, of Compound A which has an XRPD pattern substantially the same as the XRPD shown in FIG. 3, measured using CuKα radiation.

According to a further aspect of the invention, there is provided a crystalline form, Form B, of Compound A which has an XRPD pattern with at least one specific peak at 2-theta=4.3° plus or minus 0.2° 2-theta, measured using CuKα radiation.

According to the invention there is provided a crystalline form, Form B, of Compound A which has an XRPD pattern with at least one specific peak at 2-theta=16.6° plus or minus 0.2° 2-theta, measured using CuKα radiation.

According to the invention there is provided a crystalline form, Form B, of Compound A which has an XRPD pattern with at least two specific peaks at 2-theta=4.3° and 16.6° plus or minus 0.2° 2-theta, measured using CuKα radiation.

According to the invention there is provided a crystalline form, Form B, of Compound A which has an XRPD pattern with specific peaks at 2-theta=4.3, 7.7, 9.1, 11.8, 12.8, 15.9, 16.6, 18.2, 20.5, 23.4°, plus or minus 0.2° 2-theta, measured using CuKα radiation.

DSC analysis of Compound A, Form B shows a melting endotherm with an onset of 218.3° C. and a peak at 220.3° C. (FIG. 4).

Thus DSC analysis shows Compound A, Form B is a high melting solid with an onset of melting at about 218.3° C. and a peak at about 220.3° C.

When it is stated that the invention relates to a crystalline form of Compound A, Form A or Form B, the degree of crystallinity is conveniently greater than about 60%, more conveniently greater than about 80%, preferably greater than about 90% and more preferably greater than about 95%. Most preferably the degree of crystallinity is greater than about 98%.

It will be understood that the 2-theta values of the X-ray powder diffraction pattern may vary slightly from one machine to another or from one sample to another, and so the values quoted are not to be construed as absolute.

It is known that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions. Therefore it should be understood that Compound A, Form A and Form B, of the invention are not limited to the crystals that provide X-ray powder diffraction patterns identical to the X-ray powder diffraction pattern shown in FIGS. 1 and 3, and any crystals providing X-ray powder diffraction patterns substantially the same as those shown in FIGS. 1 and 3 fall within the scope of the invention. A person skilled in the art of X-ray powder diffraction is able to judge the substantial identity of X-ray powder diffraction patterns.

Persons skilled in the art of X-ray powder diffraction will understand that the relative intensity of peaks can be affected by, for example, grains above 30 microns in size and non-unitary aspect ratios, which may affect analysis of samples. The skilled person will also understand that the position of reflections can be affected by the precise height at which the sample sits in the diffractometer and the zero calibration of the diffractometer. The surface planarity of the sample may also have a small effect. Hence the diffraction pattern data presented are not to be taken as absolute values. (Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures).

Generally, a measurement error of a diffraction angle in an X-ray powder diffractogram is approximately plus or minus 0.2° 2-theta, and such degree of a measurement error should be taken into account when considering the X-ray powder diffraction pattern in FIGS. 1 and 3 and when reading Tables A and B (see Example 1). Furthermore, it should be understood that intensities might fluctuate depending on experimental conditions and sample preparation (preferred orientation).

The compounds of Formula (I) include one or more chiral centres. To the extent a structure or chemical name in this specification does not indicate chirality, the structure or name is intended to encompass any single stereoisomer (i.e. any single chiral isomer) corresponding to that structure or name, as well as any mixture of stereoisomers (e.g. a racemate). It is well-known in the art how such optically-active forms can be prepared. For example, a single stereoisomer can be obtained by isolating it from a mixtures of isomers (e.g. a racemate) using, for example, chiral chromatographic separation. In other embodiments, a single stereoisomer is obtained through direct synthesis from, for example, a chiral starting material.

Compounds of Formula (I) may for example be prepared by the reaction of a compound of Formula (II) or a salt thereof:

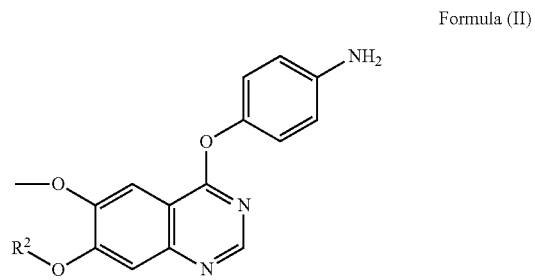

Formula (II)

where $R^2$ is as defined in any of the embodiments herein, or a protected form, with a compound of Formula (III):

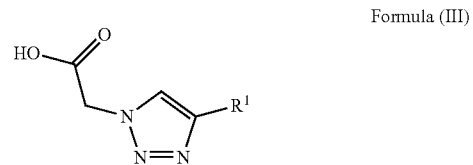

Formula (III)

or a salt thereof where $R^1$ is as defined in any of the embodiments herein, or a protected form thereof. The reaction is conveniently performed in the presence of a coupling agent (for example (1-[bis(dimethylamino)methylene]-1H-1,2,3-triazolo[4,5-b]pyridinium 3-oxid hexafluorophosphate (HATU)) in a suitable solvent (for example N,N-dimethylformamide (DMF)) and in the presence of a base (for example diisopropylethylamine (DIPEA)) at a suitable temperature (for example in the range 20-50° C. would be typical temperatures).

Compounds of Formula (II) and (III), and salts thereof, are therefore useful as intermediates in the preparation of compounds of Formula (I) and provide a further embodiment.

In any of the embodiments where a compound of Formula (II) or (III) or a salt thereof is mentioned it is to be understood that such salts do not need to be pharmaceutically acceptable salts.

The compound of Formula (II) may, for example, be prepared by reaction of a compound of Formula (IV):

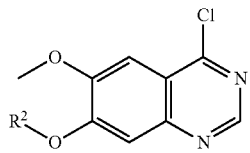

Formula (IV)

where $R^2$ is as defined in any of the embodiments herein, with 4-aminophenol. The reaction is conveniently performed in a suitable solvent (for example dimethylsulphoxide (DMSO)) in the presence of a base (for example sodium hydride) at a suitable temperature, such as room temperature.

The compound of Formula (III) may, for example, be prepared by reaction of a compound of Formula (V):

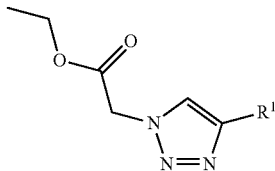

Formula (V)

where $R^1$ is as defined in any of the embodiments herein. The reaction is conveniently performed in a mixture of water and a suitable solvent (for example tetrahydrofuran (THF)) in the presence of a weak base (for example lithium hydroxide) at a suitable temperature, such as room temperature.

The compound of Formula (V) may, for example, be prepared by reaction of a compound of Formula (VI):

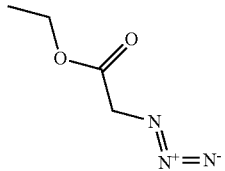

Formula (VI)

in a suitable solvent (for example acetonitrile) with

in the presence of a metal halide (for example copper (I) iodide) and a base (for example triethylamine), wherein $R^1$ is as defined in any of the embodiments herein. This reaction can be carried out in batch at a suitable temperature (for example 20° C.) for a suitable time (for example 16 h). It can also be carried out under flow conditions at a suitable temperature (for example 120° C.) for a suitable time (for example 5 minutes). A higher temperature is necessary in flow to achieve a useful reaction rate for processing large amounts of material. The intermediates are high energy compounds, but as only a small amount is being reacted at any time, the risk is minimal. The azide is then cooled to 15-40° C. for the subsequent step.

The compound of Formula (VI) may, for example, be prepared by reaction of ethyl 2-bromoacetate with an inorganic azide (for example sodium azide) in the presence of iso-propylalcohol.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. For example, compounds of Formula (I) may be converted into further compounds of Formula (I) by standard aromatic substitution reactions or by conventional functional group modifications. Such reactions and modifications include, for example, introduction of a substituent by means of an aromatic substitution reaction, reduction of substituents, alkylation of substituents and oxidation of substituents. The reagents and reaction conditions for such procedures are well known in the chemical art.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

Compounds of Formula (I), (II) and (III), and any intermediates used to make these, can be prepared by methods similar to those shown in the Examples section.

Biological Assays

The following assay was used to measure the activity of the compounds of the invention.

3 different KIT cDNA encoding for the exon11 deletion (557-558) and a secondary mutation (V654A, T670I, D816H) from Genescript were cloned into pLVX-IRES Puro vector(Clontech). Lentiviral particles were generated using Trans-lentiviral ORF packaging kit (TLP 5918) from Thermo Scientific (Waltham, Mass.) in HEK293-T/17 cells, according to the manufacturer's instructions.

Tel-KDR myc was cloned into pBCS2004, a retroviral vector, wherein KDR (K790-V1356) is fused to the C-terminus of Tel. Retroviral particles were generated in HEK293T cells. The Tel-KDR plasmid was co-transfected with helper viruses (gag-Pol and VSV-G) into HEK293T cells using calcium phosphate and the virus was harvested 72 h after transfection.

Exponentially grown Ba/F3 cells ($1.5 \times 10^6$ cells in 2 ml medium) were infected with 2 ml of viral suspension in a 6-well plate in the presence of mIL-3 (10 ng/ml) and polybrene (4 μg/ml) (Sigma Aldrich, St. Louis, Mo.) and incubated for 24 h. After 24 h, the cells were centrifuged and the viral supernatant was discarded. The cells were then re-suspended in fresh medium and allowed to recover for another day. The following day, the cells were seeded in complete medium without murine IL-3. After a week or two, when cells started proliferating, a selection was carried out by gradually increasing the puromycin concentration to 0.5 ug/ml. Once the cells were growing exponentially in puromycin, batches of cells were frozen down for banking.

The impact of KIT inhibitors on the viability of Ba/F3 expressing KIT mutations was determined using an MTS assay, which is a colorimetric sensitive quantification of viable cells in proliferation and cytotoxicity assay. In the MTS assay 3-(4,5-dimethylthiazol-2-yl)-2,5-diphenyltetrazolium bromide (MTT) in the presence of phenazine methosulfate (PMS) was used. The mitochondrial reductase forms a formazan which absorbs at 490 nm. Cells in exponential growth phase were added to 384-well plates containing pre-dispensed compounds (top concentration 10 uM, 10-point curve). The cells were incubated for 72 h at 37° C. and 5% $CO_2$. After 72 h, MTS reagent was added to the plates and incubated an additional 2 h at 37° C. before measuring the absorbance at 490 nm on a Tecan microplate reader using Magellan Software (Tecan Trading AG, Switzerland).

The absorbances were normalized as follows: (ReadDay0 control)/(Day3 control-Day0 control)*100. The $GI_{50}$ values were generated using Genedata Screener software (Genedata; Lexington, Mass.). A non-linear regression with constraints for top and bottom between 100 and −100 and no constraint on the Hill coefficient was used to generate $GI_{50}$ values. The $GI_{50}$ values reported below are the calculated mean result of at least 3 biological replicates across all the cell lines tested.

The following data was generated for the Examples:

| Example No | Ba/F3-Parental GI50 (µM) | Ba/F3-T6701 GI50 (µM) | Ba/F3-V654A GI50 (µM) | Ba/F3-D816H GI50 (µM) | TEL-KDR GI50 (µM) |
|---|---|---|---|---|---|
| 1 | 10 | 0.017 | 0.003 | 0.019 | 0.6 |
| 2 | 10 | 0.068 | 0.004 | 0.095 | 1.927 |
| 3 | 10 | 0.023 | 0.013 | 0.041 | 1.081 |
| 4 | 10 | 0.008 | 0.001 | 0.015 | 0.142 |
| 5 | 10 | 0.011 | 0.008 | 0.015 | 0.289 |
| 6 | 10 | 0.072 | 0.022 | 0.055 | 2.772 |
| 7 | 10 | 0.057 | 0.015 | 0.041 | 2.519 |
| 8 | 10 | 0.055 | 0.025 | 0.075 | 1.163 |
| 9 | 10 | 0.077 | 0.017 | 0.046 | 2.106 |
| 10 | 10 | 0.074 | 0.018 | 0.051 | 1.845 |
| 11 | 10 | 0.057 | 0.016 | 0.028 | 0.903 |
| 12 | 10 | 0.023 | 0.011 | 0.022 | 0.84 |
| 13 | 10 | 0.03 | 0.013 | 0.024 | 0.577 |

The data shows that the compounds of the invention inhibit KIT carrying both primary and secondary KIT mutations simultaneously, and furthermore, are selective against KDR.

Compounds may be further selected on the basis of further biological or physical properties which may be measured by techniques known in the art and which may be used in the assessment or selection of compounds for therapeutic or prophylactic application.

As a result of their KIT inhibitory activity, the compound of Formula (I), and pharmaceutically acceptable salts thereof are expected to be useful in therapy.

We have found that the compounds of Formula (I) possess potent anti-tumour activity which it is believed is obtained by way of inhibition of both wild type KIT and KIT mutants. We have also found that the compounds of Formula (I) may also act partly as an immune-oncology drug.

The term "therapy" is intended to have its normal meaning of dealing with a disease in order to entirely or partially relieve one, some or all of its symptoms, or to correct or compensate for the underlying pathology. The term "therapy" also includes "prophylaxis" unless there are specific indications to the contrary. The terms "therapeutic" and "therapeutically" should be interpreted in a corresponding manner.

The term "prophylaxis" is intended to have its normal meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

The term "treatment" is used synonymously with "therapy". Similarly the term "treat" can be regarded as "applying therapy" where "therapy" is as defined herein.

In one embodiment there is provided a compound of Formula (I), or a pharmaceutically acceptable salt thereof, for use in therapy.

In one embodiment there is provided the use of a compound of Formula (I), or a pharmaceutically acceptable salt thereof, for the manufacture of a medicament.

In one embodiment there is provided a compound of Formula (I), or a pharmaceutically acceptable salt thereof, for use in the treatment of a disease mediated by KIT. In one embodiment, the disease mediated by KIT is cancer. In one embodiment the cancer is selected from the group consisting of gastrointestinal stromal tumor (GIST), melanoma, lung cancers, glioblastoma, leukemias, testicular carcinomas and head and neck cancers. Lung cancers include small cell lung cancer (SCLC), adenocarcinomas and squamous carcinomas of the lung. Leukemias include acute myeloid leukaemia (AML) and mast cell leukemias.

In one embodiment the cancer is a gastrointestinal stromal tumor. GIST is a type of tumor that occurs in the gastrointestinal tract, most commonly in the stomach or small intestine In one embodiment there is provided a compound of Formula (I), or a pharmaceutically acceptable salt thereof, for use in the treatment of cancer.

In one embodiment there is provided the use of the compound of Formula (I), or a pharmaceutically acceptable salt thereof, for the manufacture of a medicament for the treatment of a disease mediated by KIT. In one embodiment, the disease mediated by KIT is cancer. In one embodiment, the cancer is selected from the group consisting of a gastrointestinal stromal tumor (GIST), melanoma, lung cancers, glioblastoma, leukemias, testicular carcinomas and head and neck cancers. Lung cancers include small cell lung cancer (SCLC), adenocarcinomas and squamous carcinomas of the lung. Leukemias include acute myeloid leukaemia (AML) and mast cell leukemias. In one embodiment the cancer is a gastrointestinal stromal tumor.

In one embodiment there is provided the use of the compound of Formula (I), or a pharmaceutically acceptable salt thereof, for the manufacture of a medicament for the treatment of cancer.

In one embodiment there is provided a method for treating a disease in which inhibition of KIT is beneficial in a warm-blooded animal in need of such treatment, which comprises administering to said warm-blooded animal a therapeutically effective amount of a compound of Formula (I), or a pharmaceutically acceptable salt thereof. In one embodiment, the disease is cancer. In one embodiment, the cancer is selected from the group consisting of gastrointestinal stromal tumor (GIST), melanoma, lung cancers, glioblastoma, leukemias, testicular carcinomas and head and neck cancers. Lung cancers include small cell lung cancer (SCLC), adenocarcinomas and squamous carcinomas of the lung. Leukemias include acute myeloid leukaemia (AML) and mast cell leukemias.

In one embodiment the cancer is a gastrointestinal stromal tumor.

The term "therapeutically effective amount" refers to an amount of a compound of Formula (I) as described in any of the embodiments herein which is effective to provide "therapy" in a subject, or to "treat" a disease or disorder in a subject. In the case of cancer, the therapeutically effective amount may cause any of the changes observable or measurable in a subject as described in the definition of "therapy", "treatment" and "prophylaxis" above. For example, the effective amount can reduce the number of cancer or tumour cells; reduce the overall tumour size; inhibit or stop tumour cell infiltration into peripheral organs including, for example, the soft tissue and bone; inhibit and stop tumour metastasis; inhibit and stop tumour growth; relieve to some extent one or more of the symptoms associated with the cancer; reduce morbidity and mortality; improve quality of life; or a combination of such effects. An effective amount may be an amount sufficient to decrease the symptoms of a disease responsive to inhibition of KIT activity. For cancer therapy, efficacy in-vivo can, for example, be measured by assessing the duration of survival, time to disease progression (TTP), the response rates (RR), duration of response, and/or quality of life. As recognized by those skilled in the art, effective amounts may vary depending on route of administration, excipient usage, and co-usage with other agents. For example, where a combination therapy is used, the amount of the compound of Formula (I) or pharmaceutically acceptable salt described in this specification and the amount of the other pharmaceutically active agent(s) are, when combined, jointly effective to treat a targeted disorder in the animal patient. In this context, the combined amounts are in a "therapeutically effective amount" if they are, when combined, sufficient to decrease the symptoms of a disease responsive to inhibition of KIT activity as described above. Typically, such amounts may be determined by one skilled in the art by, for example, starting with the dosage range described in this specification for the compound of Formula (I) or pharmaceutically acceptable salt thereof and an approved or otherwise published dosage range(s) of the other pharmaceutically active compound(s).

"Warm-blooded animals" include, for example, humans.

In one embodiment there is provided a method for treating cancer in a warm-blooded animal in need of such treatment, which comprises administering to said warm-blooded animal a therapeutically effective amount of a compound of Formula (I), or a pharmaceutically acceptable salt thereof. In one embodiment, the cancer is selected from the group consisting of gastrointestinal stromal tumor (GIST), melanoma, lung cancers, glioblastoma, leukemias, testicular carcinomas and head and neck cancers. Lung cancers include small cell lung cancer (SCLC), adenocarcinomas and squamous carcinomas of the lung. Leukemias include acute myeloid leukaemia (AML) and mast cell leukemias.

In one embodiment the cancer is a gastrointestinal stromal tumor.

The anti-cancer treatment described in this specification may be useful as a sole therapy, or may involve, in addition to administration of the compound of Formula (I), or a pharmaceutically acceptable salt thereof, conventional surgery, radiotherapy or chemotherapy; or a combination of such additional therapies. Such conventional surgery, radiotherapy or chemotherapy may be administered simultaneously, sequentially or separately to treatment with the compound of Formula (I) or a pharmaceutically acceptable salt thereof.

Where a combination therapy is administered "simultaneously", this includes treatment of a patient with a single dosage form (e.g. a tablet) comprising both a compound of Formula (I), or a pharmaceutically acceptable salt thereof and an additional anti-cancer substance; and also simultaneous dosing of separate dosage forms each separately comprising one of the respective combination partners.

Where a combination therapy is administered "sequentially" or "separately", this includes treatment of a patient with a first dosage form (e.g. a tablet) comprising a compound of Formula (I), or a pharmaceutically acceptable salt thereof, followed by treatment of the same patient with a second dosage form comprising an additional anti-cancer substance; or treatment of a patient with a single dosage form (e.g. a tablet) comprising a particular anti-cancer substance, followed by treatment of the same patient with a second dosage form comprising a compound of Formula (I), or a pharmaceutically acceptable salt thereof. The interval between the sequential or separate doses may be judged by a skilled practitioner with reference to the information in this specification.

In one embodiment there is provided a compound of Formula (I), or a pharmaceutically acceptable salt thereof, for use in the treatment of cancer, where the compound of Formula (I), or a pharmaceutically acceptable salt thereof is administered before surgery.

Administration of a compound of Formula (I), or a pharmaceutically acceptable salt thereof, before surgery to entirely or partially remove a cancer may be referred to as "neo-adjuvant therapy". In such a scenario, the goal of administering the compound of Formula (I), or a pharmaceutically acceptable salt thereof is generally to reduce the size of the target tumour in order to increase the chances of a successful resection. As such, the length of time the compound of Formula (I), or a pharmaceutically acceptable salt thereof is dosed before surgery may be judged by a skilled practitioner with reference to the information within this specification.

In one embodiment there is provided a compound of Formula (I), or a pharmaceutically acceptable salt thereof, for use in the treatment of cancer, where the compound of Formula (I), or a pharmaceutically acceptable salt thereof is administered after surgery.

In one embodiment there is provided a compound of Formula (I), or a pharmaceutically acceptable salt thereof, for use in the treatment of cancer, where the compound of Formula (I), or a pharmaceutically acceptable salt thereof is administered in combination with at least one additional anti-cancer substance.

In one embodiment there is provided a compound of Formula (I), or a pharmaceutically acceptable salt thereof, for use in the treatment of cancer, where the compound of Formula (I), or a pharmaceutically acceptable salt thereof is administered simultaneously, sequentially or separately with at least one additional anti-cancer substance. Such anti-cancer substances may include one or more of the following categories of anti-tumour agents:

(i) inhibitors of growth factor function and their downstream signalling pathways: included are Ab modulators of any growth factor or growth factor receptor targets, reviewed by Stern et al. Critical Reviews in Oncology/Haematology, 2005, 54, pp11-29); also included are small molecule inhibitors of such targets, for example kinase inhibitors—examples include the anti-erbB2 antibody trastuzumab [Herceptin™], the anti-EGFR antibody panitumumab, the anti-EGFR antibody cetuximab [Erbitux, C225] and tyrosine kinase inhibitors including inhibitors of the erbB receptor family, such as epidermal growth factor family receptor (EGFR/erbB1) tyrosine kinase inhibitors such as gefitinib or erlotinib, erbB2 tyrosine kinase inhibitors such as lapatinib, and mixed erb1/2 inhibitors such as afatanib; similar strategies are available for other classes of growth factors and their receptors, for example inhibitors of the hepatocyte growth factor family or their receptors including c-met and ron; inhibitors of the insulin and insulin growth factor family or their receptors (IGFR, IR) inhibitors of the platelet-derived growth factor family or their receptors (PDGFR), and inhibitors of signalling mediated by other receptor tyrosine kinases such as c-kit, AnLK, and CSF-1R; also included are modulators which target signalling proteins in the PI3-kinase signalling pathway, for example, inhibitors of PI3-kinase isoforms such as PI3K-α/β/γ and ser/thr kinases such as AKT, mTOR (such as AZD2014), PDK, SGK, PI4K or PIP5K; also included are inhibitors of serine/threonine kinases not listed above, for example raf inhibitors such as vemurafenib, MEK inhibitors such as selumetinib (AZD6244), Abl inhibitors such as imatinib or nilotinib, Btk inhibitors such as ibrutinib, Syk inhibitors such as fostamatinib, aurora kinase inhibitors (for example AZD1152), inhibitors of other ser/thr kinases such as JAKs, STATs and IRAK4, and cyclin dependent kinase inhibitors for example inhibitors of CDK1, CDK7, CDK9 and CDK4/6 such as palbociclib;

(ii) modulators of apoptotic and cell death pathways such as Bcl family modulators (e.g. ABT-263/Navitoclax, ABT-199);

(iii) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies. Specific examples include monoclonal antibodies targeting PD-1 (e.g. BMS-936558) or CTLA4 (e.g. ipilimumab and tremelimumab).

Therefore, in one embodiment there is provided a compound of Formula (I), or a pharmaceutically acceptable salt thereof, and at least one additional anti-tumour substance, for use in the treatment of cancer. In one embodiment there is provided a compound of Formula (I), or a pharmaceutically acceptable salt thereof, for use in the treatment of cancer, where the compound of Formula (I), or a pharmaceutically acceptable salt thereof is administered in combination with an additional anti-tumour substance. In one embodiment there is one additional anti-tumour substance. In one embodiment there are two additional anti-tumour substances. In one embodiment there are three or more additional anti-tumour substances.

In one embodiment there is provided a compound of Formula (I), or a pharmaceutically acceptable salt thereof, and at least one additional anti-tumour substance for use in the simultaneous, separate or sequential treatment of cancer. In one embodiment there is provided a compound of Formula (I), or a pharmaceutically acceptable salt thereof, for use in the treatment of cancer, where the compound of Formula (I), or a pharmaceutically acceptable salt thereof, is administered simultaneously, separately or sequentially with an additional anti-tumour substance.

In one embodiment there is provided a method of treating cancer in a warm-blooded animal who is in need of such treatment, which comprises administering to said warm-blooded animal a compound of Formula (I), or a pharmaceutically acceptable salt thereof and at least one additional anti-tumour substance, wherein the amounts of the compound of Formula (I), or a pharmaceutically acceptable salt thereof, and the additional anti-tumour substance are jointly effective in producing an anti-cancer effect.

In one embodiment there is provided a method of treating cancer in a warm-blooded animal who is in need of such treatment, which comprises administering to said warm-blooded animal a compound of Formula (I), or a pharmaceutically acceptable salt thereof, and simultaneously, separately or sequentially administering at least one additional anti-tumour substance to said warm-blooded animal, wherein the amounts of the compound of Formula (I), or pharmaceutically acceptable salt thereof, and the additional anti-tumour substance are jointly effective in producing an anti-cancer effect.

In any embodiment the additional anti-tumour substance is selected from the group consisting of one or more of the anti-tumour substances listed under points (i)-(iii) above.

In one embodiment there is provided a pharmaceutical composition comprising a compound of Formula (I) and at least one additional anti-tumour substance, for use in the treatment of cancer. In one embodiment the pharmaceutical composition also comprises at least one pharmaceutically acceptable diluent or carrier. In one embodiment the anti-tumour substance is an anti-neoplastic agent.

According to a further embodiment there is provided a kit comprising:

a) A compound of Formula (I), or a pharmaceutically acceptable salt thereof, in a first unit dosage form;

b) A further additional anti-tumour substance in a further unit dosage form;

c) Container means for containing said first and further unit dosage forms; and optionally d) Instructions for use.

The compounds of Formula (I), and pharmaceutically acceptable salts thereof, may be administered as pharmaceutical compositions, comprising one or more pharmaceutically acceptable diluents or carriers.

Therefore, in one embodiment there is provided a pharmaceutical composition comprising a compound of Formula (I), or a pharmaceutically acceptable salt thereof, and at least one pharmaceutically acceptable diluent or carrier. The compositions may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous or intramuscular dosing), or as a suppository for rectal dosing. The compositions may be obtained by conventional procedures using conventional pharmaceutical excipients, well known in the art. Thus, compositions intended for oral use may contain, for example, one or more colouring, sweetening, flavouring and/or preservative agents.

In one embodiment there is provided a pharmaceutical composition comprising a compound of Formula (I), or a pharmaceutically acceptable salt thereof, and at least one pharmaceutically acceptable diluent or carrier, for use in therapy.

In one embodiment there is provided a pharmaceutical composition comprising a compound of Formula (I), or a pharmaceutically acceptable salt thereof, and at least one pharmaceutically acceptable diluent or carrier, for use in the treatment of cancer. In one embodiment, said cancer is selected from the group consisting of gastrointestinal stromal tumor (GIST), melanoma, lung cancers, glioblastoma, leukemias, testicular carcinomas and head and neck cancers. Lung cancers include small cell lung cancer (SCLC), adenocarcinomas and squamous carcinomas of the lung. Leukemias include acute myeloid leukaemia (AML) and mast cell leukemias.

The compound of Formula (I) will normally be administered to a warm-blooded animal at a unit dose within the range 2.5-5000 mg/m² body area of the animal, or approximately 0.05-100 mg/kg, and this normally provides a therapeutically-effective dose. A unit dose form such as a tablet or capsule will usually contain, for example 0.1-500 mg of active ingredient. The daily dose will necessarily be varied depending upon the host treated, the particular route of administration, any therapies being co-administered, and the severity of the illness being treated. Accordingly the practitioner who is treating any particular patient may determine the optimum dosage.

EXAMPLES

Aspects of the present disclosure can be further defined by reference to the following non-limiting examples, which describe in detail preparation of certain compounds and intermediates of the present disclosure and methods for using compounds of the present disclosure. It will be apparent to those skilled in the art that many modifications, both to materials and methods, can be practiced without departing from the scope of the present disclosure.

Unless stated otherwise:

(i) all syntheses were carried out at ambient temperature, i.e. in the range 17 to 25° C. and under an atmosphere of an inert gas such as nitrogen unless otherwise stated;

(ii) evaporations were carried out by rotary evaporation, utilising Genevac equipment or Biotage v10 evaporator in vacuo and work up procedures were carried out after removal of residual solids by filtration;

(iii) flash column chromatography was performed on one of the following: Merck Kieselgel silica (Art. 9385), on reversed phase silica (Fluka silica gel 90 C18), Silicycle cartridges (40-63 μm silica, 4 to 330 g weight), on Grace resolv cartridges (4-120 g), on RediSep Rf 1.5 Flash columns, on RediSep Rf high performance Gold Flash columns (150-415 g weight), on RediSep Rf Gold C18 Reversed-phase columns (20-40 μm silica), either manually or automated using an Isco CombiFlash Companion system or similar system;

(iv) preparative reverse phase HPLC was performed on a Waters instrument (600/2700 or 2525) fitted with a ZMD or ZQ ESCi mass spectrometers and a Waters X-Terra, a Waters X-Bridge or a Waters SunFire reverse-phase column (C-18, 5 microns silica, 19 mm or 50 mm diameter, 100 mm length, flow rate of 40 ml/minute) using decreasingly polar mixtures of water (containing 1% ammonia) and acetonitrile or decreasingly polar mixtures of water (containing 0.1% formic acid) and acetonitrile as eluents;

(v) chiral HPLC methods were carried out using a Gilson GX-281 HPLC and a Daicel CHIRALPAK IC (2×25 cm, 5um) or Daicel CHIRALPAK IF (2×25 cm, 5 um); in general a flow rate of between 10-350 ml/minute and detection was by UV absorbance at a typical wavelength of 254 nm. A sample concentration of about 1-100 mg/ml was used in a suitable solvent mixture with an injection volume of between 0.5-10 ml and run time of between 10-150 minutes and a typical oven temperature of 25-35° C.; analytical chiral HPLC methods were carried out using Shimadzu UFLC and a Daicel CHIRALPAK IC-3 (50×4.6 mm 3 um) or Daicel CHIRALPAK IF-3 (50×4.6 mm 3 um); in general a flow rate of 1 ml/minute and detection was by UV absorbance at a typical wavelength of 254 nm. A sample concentration of about 1 mg/ml was used in a suitable solvent such as ethanol with an injection volume of about 10 μl and run time of between 10-60 minutes and a typical oven temperature of 25-35° C.;

(vi) yields, where present, are not necessarily the maximum attainable;

(vii) in general, the structures of compounds of Formula (I) were confirmed by nuclear magnetic resonance (NMR) spectroscopy; NMR chemical shift values were measured on the delta scale [proton magnetic resonance spectra were determined using a Bruker Avance 500 (500 MHz), Bruker Avance 400 (400 MHz), Bruker Avance 300 (300 MHz) or Bruker DRX (300 MHz) instrument]; measurements were taken at ambient temperature unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal;

(viii) in general, compounds of Formula (I) were also characterized by mass spectroscopy following liquid chromatography (LCMS or UPLC); in general, reverse-phase C18 silica was used with a flow rate of 1 mL/minute and detection was by Electrospray Mass Spectrometry and by UV absorbance recording a wavelength range of 220-320 nm. Analytical UPLC was performed on CSH C18 reverse-phase silica, using a Waters XSelect CSH C18 column with dimensions 2.1×50 mm and particle size 1.7 micron). Gradient analysis was employed using decreasingly polar mixtures as eluent, for example decreasingly polar mixtures of water (containing 0.1% formic acid or 0.1% ammonia) as solvent A and acetonitrile as solvent B. A typical 2 minute analytical UPLC method would employ a solvent gradient over 1.3 minutes, at approximately 1 mL per minute, from a 97:3 mixture of solvents A and B respectively to a 3:97 mixture of solvents A and B. The reported molecular ion corresponds to the $[M+H]^+$ unless otherwise specified; for molecules with multiple isotopic patterns (Br, Cl, etc.) the reported value is the one obtained for the lowest isotope mass unless otherwise specified;

(ix) ion exchange purification was generally performed using an SCX-2 (Biotage) cartridge;

(x) where reactions refer to the use of a microwave, one of the following microwave reactors were used: Biotage Initiator, Personal Chemistry Emrys Optimizer, Personal Chemistry Smithcreator or CEM Explorer;

(xi) intermediate purity was assessed by thin layer chromatographic, mass spectroscopy, LCMS, UPLC/MS, HPLC and/or NMR analysis; and (xii) the following abbreviations have been used:
DCM dichloromethane
DIPEA diisopropylethylamine
DMF N,N-dimethylformamide
DMSO dimethylsulfoxide
e.e. enantiomeric excess HATU (1-[bis(dimethylamino)methylene]-1H-1,2,3-triazolo[4,5-b]pyridinium 3-oxid hexafluorophosphate)
HCl hydrochloric acid
HPLC high performance liquid chromatography
NMP N-methylpyrrolidone
NMR nuclear magnetic resonance
tR retention time (xiii) For XRPD analysis the instrument used was a Bruker D4

The X-ray powder diffractogram was determined by mounting a sample of the crystalline material on a Bruker single silicon crystal (SSC) wafer mount and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5418 angstroms. The collimated X-ray source was passed through an automatic variable divergence slit set at V20 and the reflected radiation directed through a 5.89 mm anti scatter slit and a 9.55 mm detector slit. Samples were measured in reflection geometry in θ-2θ configuration over the scan range 2° to 40° 2θ with a nominal 0.12 second exposure per 0.02° increment. The instrument was equipped with a Position sensitive detector (Lynxeye). Persons skilled in the art of X-ray powder diffraction will understand that the relative intensity of peaks can be affected by, for example, grains above 30 microns in size and non-unitary aspect ratios that may affect analysis of samples. The skilled person will also understand that the position of reflections can be affected by the precise height at which the sample sits in the diffractometer and the zero calibration of the diffractometer. The surface planarity of the sample may also have a small effect. Hence the diffraction pattern data presented are not to be taken as absolute values;

(xiv) For the Differential Scanning Calorimetry the instrument used was TA Instruments Q2000 DSC Typically less than 3 mg of material contained in a standard aluminium pan fitted with a lid was heated over the temperature range 25° C. to 300° C. at a constant heating rate of 10° C. per minute. A purge gas using nitrogen was used—flow rate 50 ml per minute. Thermal data was analysed using standard software, e.g., Universal v.4.5A from TA INSTRUMENTS®;

(xv) For the Thermogravimetry Analysis (TGA) the instrument used was TA Instruments Q5000 TGA Typically less than 5 mg was placed into an aluminum sample pan and transferred to the TGA furnace. The instrument was purged with nitrogen at 50 mL/min and data collected between 25° C. and just below the melting point of the compound, using a constant heating rate of 10° C./minute. Thermal data was analyzed using standard software, e.g., Universal v.4.5A from TA INSTRUMENTS®.

Example 1

N-(4-((6,7-Dimethoxyquinazolin-4-yl)oxy)phenyl)-2-(4-isopropyl-1H-1,2,3-triazol-1-yl)acetamide

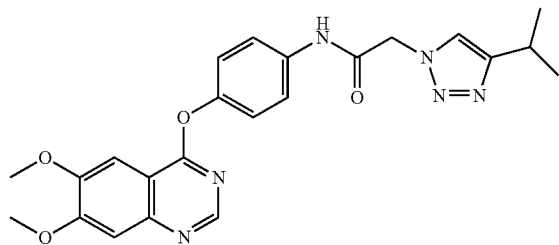 [SMILES: COc1cc2ncnc(Oc3ccc(NC(=O)Cn4cc(C(C)C)nn4)cc3)c2cc1OC]

HATU (8.4 g, 22.1 mmol) was added as a solution in DMF (30 mL) to a suspension of 4-((6,7-dimethoxyquinazolin-4-yl)oxy)aniline (5.1 g, 17 mmol), 45% strength 2-(4-isopropyl-1H-1,2,3-triazol-1-yl)acetic acid (7.7 g, 20.4 mmol) and DIPEA (8.9 ml, 51 mmol) in DMF (120 mL) at ambient temperature. The mixture was sonicated to aid solubility then stirred at ambient temperature for 16 hours. The mixture was poured into water (1500 mL), adjusted to pH 8 with NaHCO$_3$ solution and extracted with ethyl acetate (4×400 mL). The combined organic extracts were washed with water (2×400 mL) and saturated brine (250 mL), dried, filtered and evaporated to dryness. The crude product was purified by flash silica chromatography, elution gradient 2 to 4% (10:1 methanol/conc. NH3 (aq.)) in DCM. Appropriate fractions were diluted with ethyl acetate (250 mL) and concentrated under vacuum until solid began to crystallise from solution (around 250 mL volume). Ethyl acetate (200 mL) was added and the mixture concentrated to around 250 mL volume. Ethyl acetate (100 mL) was added and the resulting suspension sonicated, warmed to 55° C. and allowed to cool to ambient temperature with stirring. The resulting solid was collected by filtration, washed with ethyl acetate (50 ml) and dried to give 5.5 g of pure product, containing ethyl acetate. The solid was recrystallised from hot acetonitrile (~150 ml) and allowed to cool to ambient temperature with stirring. The solid was collected by filtration, washed with cold acetonitrile and dried under vacuum at 50° C. to afford the title compound as a white crystalline solid (3.7 g, 48%). $^1$H NMR (500 MHz, DMSO, 27° C.) δ 1.25 (6H, d), 2.99 (1H, hept), 3.96 (3H, s), 3.98 (3H, s), 5.28 (2H, s), 7.28 (2H, d), 7.37 (1H, s), 7.55 (1H, s), 7.67 (2H, d), 7.87 (1H, d), 8.53 (1H, s), 10.55 (1H, s). m/z: ES+[M+H]+449.

The intermediates used in Example 1 were prepared as follows:

Preparation of 4-((6,7-Dimethoxyquinazolin-4-yl)oxy)aniline

60% Sodium hydride dispersion (2 g, 49 mmol) was added portionwise to DMSO (80 mL) at 22° C. under nitrogen. The resulting slurry was stirred at ambient temperature for 10 minutes. 4-Aminophenol (5.3 g, 49 mmol) was added to the mixture at 22-28° C. under nitrogen and the resulting grey slurry was stirred at ambient temperature for 10 minutes. 4-Chloro-6,7-dimethoxyquinazoline (10 g, 44.5 mmol) was added to the mixture at 22-28° C. under nitrogen and the resulting red slurry was stirred at ambient temperature for 1 hour. The reaction mixture was poured into stirred water (1200 ml). The resulting precipitate was collected by filtration, washed with water (2×400 ml) then heptane (400 ml) and air dried to afford the title compound (12.6 g, 95%) as a beige solid. $^1$H NMR (500 MHz, DMSO, 27° C.) δ 3.95 (3H, s), 3.96 (3H, s), 5.05 (2H, s), 6.61 (2H, d), 6.91 (2H, d), 7.34 (1H, s), 7.51 (1H, s), 8.50 (1H, s). m/z: ES+[M+H]+ 298.

Preparation of Ethyl 2-(4-isopropyl-1H-1,2,3-triazol-1-yl)acetate

30% Ethyl 2-azidoacetate in DCM (19.5 g, 45.4 mmol) was added as a solution in acetonitrile (27 mL) over 5 minutes to a suspension of copper(I) iodide (0.17 g, 0.91 mmol), 3-methylbut-1-yne (5.1 mL, 49.9 mmol) and triethylamine (0.13 mL, 0.9 mmol) in acetonitrile (27 ml) at ambient temperature. The mixture was stirred for 3 days at ambient temperature. The mixture was concentrated and the residue was partitioned between water (150 ml) and ethyl acetate (150 mL). The aqueous layer was extracted with ethyl acetate (100 ml) and the extracts combined with the organic layer. The combined extracts were dried and evaporated to dryness. The crude product was purified by flash silica chromatography, elution gradient 30 to 50% ethyl acetate in heptane. Pure fractions were evaporated to dryness to afford the title compound as a white crystalline solid (8.1 g, 90%). $^1$H NMR (500 MHz, DMSO, 27° C.) δ 1.21 (3H, t), 1.22 (6H, d), 2.98 (1H, hept), 4.16 (2H, q), 5.30 (2H, s), 7.82 (1H, d); m/z: ES+ [M+H]+ 198.

Preparation of 2-(4-Isopropyl-1H-1,2,3-triazol-1-yl)acetic acid

Lithium hydroxide hydrate (10.2 g, 242.5 mmol) in water (540 mL) was added to a solution of ethyl 2-(4-isopropyl-1H-1,2,3-triazol-1-yl)acetate (15.9 g, 80.8 mmol) in THF (180 mL). The mixture was stirred for 90 minutes, then concentrated to a volume such that the organic solvents had been removed. The resulting aqueous solution was acidified to pH 5 with 2M HCl and extracted with ethyl acetate (200 mL). The aqueous layer was evaporated to dryness to afford the title compound as a white solid containing LiCl (28.2 g, 100%, 48% strength), which was used without further purification. $^1$H NMR (500 MHz, DMSO, 27° C.) δ 1.20 (6H, d), 2.92 (1H, hept), 4.59 (2H, s), 7.62 (1H, d); m/z: ES+ [M+H]+ 170.

Form A

The final product, N-(4-((6,7-dimethoxyquinazolin-4-yl)oxy)phenyl)-2-(4-isopropyl-1H-1,2,3-triazol-1-yl)acetamide, was analysed by XRPD and DSC and found to be crystalline. XRPD of a sample of the material gave rise to a diffraction pattern as shown in FIG. 1. N-(4-((6,7-dimethoxyquinazolin-4-yl)oxy)phenyl)-2-(4-isopropyl-1H-1,2,3-triazol-1-yl)acetamide, Form A is characterised by at least one peak at a 2θ value of 4.7° or 8.9°, measured using CuKα radiation. The ten most prominent peaks of the XRPD are shown in Table A.

TABLE A

Ten most Prominent XRPD peaks for Form A,
N-(4-((6,7-dimethoxyquinazolin-4-yl)oxy)phenyl)-
2-(4-isopropyl-1H-1,2,3-triazol-1-yl)acetamide

| Angle 2-Theta (2θ) | Intensity % |
|---|---|
| 7.6 | 100 |
| 20.5 | 29.3 |
| 15.9 | 27.9 |
| 23.3 | 22.9 |
| 22.9 | 21.3 |
| 15.3 | 21.2 |
| 11.9 | 20.9 |
| 8.9 | 16.5 |
| 4.7 | 16.2 |
| 20.0 | 12.5 | wherein the 2-theta values are +/−0.2°.

A trace of the DSC of N-(4-((6,7-dimethoxyquinazolin-4-yl)oxy)phenyl)-2-(4-isopropyl-1H-1,2,3-triazol-1-yl)acetamide, Form A is shown in FIG. 2.

Form B

Form B material was produced by slurrying N-(4-((6,7-dimethoxyquinazolin-4-yl)oxy)phenyl)-2-(4-isopropyl-1H-1,2,3-triazol-1-yl)acetamide, Form A in water at room temperature. Approximately 10 mg of material was placed in a 1.5 ml glass vial with a magnetic stirrer bar, and approximately 0.5 ml of water added. The vial was then sealed tightly with a cap and left to stir on a magnetic stirrer plate. After approximately 3 days, the sample was removed from the plate, the cap taken off and the slurry left to dry under ambient conditions before it was analysed by XRPD, DSC and TGA. The resultant material (Form B) was determined to be crystalline by XRPD. This material had a melting point of 203.8° C. (onset). The material showed a decrease in weight of 0.4% after heating from 25° C. to 200° C., suggesting that Form B is anhydrous.

A trace of the DSC of N-(4-((6,7-dimethoxyquinazolin-4-yl)oxy)phenyl)-2-(4-isopropyl-1H-1,2,3-triazol-1-yl)acetamide, Form B is shown in FIG. 4.

XRPD of a sample of the material gave rise to a diffraction pattern as shown in FIG. 3. N-(4-((6,7-dimethoxyquinazolin-4-yl)oxy)phenyl)-2-(4-isopropyl-1H-1,2,3-triazol-1-yl)acetamide, Form B is characterised by at least one peak at a 2θ value of 4.3° or 16.6°, measured using CuKα radiation. The ten most prominent peaks of the XRPD are shown in Table B.

TABLE B

Ten most Prominent XRPD peaks for Form B, N-(4-
((6,7-dimethoxy quinazolin-4-yl)oxy)phenyl)-2-
(4-isopropyl-1H-1,2,3-triazol-1-yl)acetamide

| Angle 2-Theta (2θ) | Intensity % |
|---|---|
| 16.6 | 100 |
| 7.7 | 67.8 |
| 18.2 | 62.3 |
| 4.3 | 49.2 |
| 20.5 | 39.7 |
| 11.8 | 35.7 |
| 23.4 | 33.7 |
| 15.9 | 33 |
| 9.1 | 32.8 |
| 12.8 | 31.4 | wherein the 2-theta values are +/−0.2°.

Example 2

2-(4-Cyclopropyl-1H-1,2,3-triazol-1-yl)-N-(4-((6,7-dimethoxyquinazolin-4-yl)oxy)phenyl)acetamide

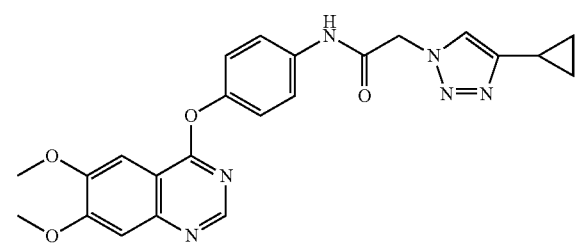 [SMILES: COc1cc2ncnc(Oc3ccc(NC(=O)Cn4cc(C5CC5)nn4)cc3)c2cc1OC]

HATU (249 mg, 0.7 mmol) was added to a solution of 4-((6,7-dimethoxyquinazolin-4-yl)oxy)aniline (150 mg, 0.5 mmol), 2-(4-cyclopropyl-1H-1,2,3-triazol-1-yl)acetic acid (93 mg, 0.6 mmol) and DIPEA (0.26 mL, 1.5 mmol) in DMF (7 mL) at ambient temperature. The mixture was stirred at ambient temperature for 5 hours. The mixture was poured into water (50 mL) and extracted with ethyl acetate (3×50 mL). The combined organic extracts were washed with saturated brine (50 mL) and dried, filtered and evaporated to dryness. The crude product was purified by flash silica chromatography, elution gradient 2 to 4% (10:1 methanol/conc. NH$_3$ (aq)) in DCM. Pure fractions were evaporated to dryness and the residue triturated with diethyl ether to afford the title compound as a white crystalline solid (181 mg, 80%). $^1$H NMR (500 MHz, DMSO, 27° C.) δ 0.69-0.75 (2H, m), 0.87-0.94 (2H, m), 1.97 (1H, tt), 3.96 (3H, s), 3.98 (3H, s), 5.25 (2H, s), 7.28 (2H, d), 7.37 (1H, s), 7.55 (1H, s), 7.66 (2H, d), 7.86 (1H, s), 8.53 (1H, s), 10.53 (1H, s); m/z: ES+ [M+H]+ 447.

Example 3

N-(4-((6,7-Dimethoxyquinazolin-4-yl)oxy)-2-methoxyphenyl)-2-(4-isopropyl-1H-1,2,3-triazol-1-yl)acetamide

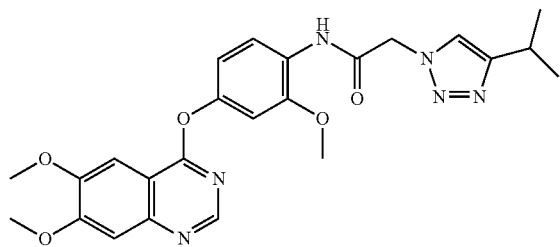 [SMILES: COc1cc(Oc2ncnc3cc(OC)c(OC)cc23)ccc1NC(=O)Cn1cc(C(C)C)nn1]

HATU (0.2 g, 0.5 mmol) was added to a solution of 4-((6,7-dimethoxyquinazolin-4-yl)oxy)-2-methoxyaniline (0.1 g, 0.3 mmol), 2-(4-isopropyl-1H-1,2,3-triazol-1-yl)acetic acid (0.19 g, 0.5 mmol) and DIPEA (0.16 mL, 0.9 mmol) in DMF (4 mL) at ambient temperature. The mixture was stirred at ambient temperature for 1 hour. Water (5 mL) was added and the mixture was stirred at ambient temperature for 3 days. The mixture was basified with 2M $K_2CO_3$ (50 mL) and extracted with DCM (70 mL). The organic layer was washed with water (2×40 mL), brine (40 mL), dried and evaporated to dryness. The crude product was purified by flash silica chromatography, elution gradient 1 to 6% (1M $NH_3$ in methanol) in DCM. Pure fractions were evaporated to dryness to afford the title compound as a yellow semi-crystalline solid (0.08 g, 55%). $^1$H NMR (500 MHz, DMSO, 27° C.) δ 1.24 (6H, d), 2.99 (1H, dq), 3.85 (3H, s), 3.96 (3H, s), 3.98 (3H, s), 5.37 (2H, s), 6.86 (1H, dd), 7.10 (1H, d), 7.37 (1H, s), 7.54 (1H, s), 7.86 (1H, s), 7.97 (1H, d), 8.55 (1H, s), 9.74 (1H, s). m/z: ES+ [M+H]+ 479.

Preparation of 4-((6,7-dimethoxyquinazolin-4-yl)oxy)-2-methoxyaniline

60% Sodium hydride dispersion (0.11 g, 2.7 mmol) was added portionwise to DMSO (3 mL) at 22° C. under nitrogen. The resulting slurry was stirred at ambient temperature for 5 minutes. 4-Amino-3-methoxyphenol (0.37 g, 2.7 mmol) was added to the mixture at 22-28° C. under nitrogen and the resulting grey slurry was stirred at ambient temperature for 5 minutes. 4-Chloro-6,7-dimethoxyquinazoline (0.5 g, 2.2 mmol) was added to the mixture at 22-28° C. under nitrogen. The resulting dark mixture was stirred at 60° C. for 30 minutes then at ambient temperature for 3 hours. Water (40 mL) was added to the mixture. The resulting precipitate was collected by filtration and washed with water (2×10 mL). The solid was treated with methanol (5 mL) and evaporated to afford the title compound as a grey solid (0.54 g, 75%), which was used without further purification. $^1$H NMR (500 MHz, DMSO, 27° C.) δ 3.74 (3H, s), 3.96 (6H, d), 4.67 (2H, s), 6.59 (1H, dd), 6.67 (1H, d), 6.76 (1H, d), 7.35 (1H, s), 7.51 (1H, s), 8.51 (1H, s). m/z: ES+ [M+H]+ 328.

Example 4

N-(4-((6,7-Dimethoxyquinazolin-4-yl)oxy)-3-fluorophenyl)-2-(4-isopropyl-1H-1,2,3-triazol-1-yl)acetamide

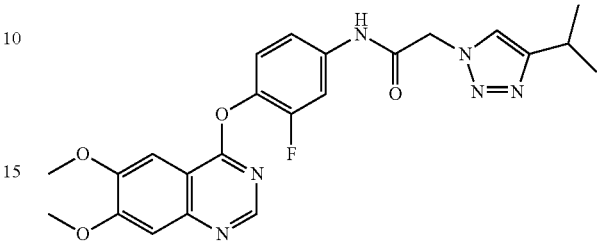

HATU (289 mg, 0.8 mmol) was added to 2-(4-isopropyl-1H-1,2,3-triazol-1-yl)acetic acid (86 mg, 0.5 mmol), 4-((6,7-dimethoxyquinazolin-4-yl)oxy)-3-fluoroaniline (160 mg, 0.5 mmol) and DIPEA (0.18 mL, 1 mmol) in DMF (10 mL) under nitrogen. The resulting mixture was stirred at 25° C. for 2 h. The crude product was purified by preparative HPLC. Fractions containing the desired compound were evaporated to dryness to afford the title compound as a white solid (85 mg, 36%). $^1$H NMR (300 MHz, DMSO, 21°) δ 1.25 (6H, d), 3.00 (1H, p), 3.98 (6H, d), 5.31 (2H, s), 7.31-7.53 (3H, m), 7.56 (1H, s), 7.76 (1H, dd), 7.89 (1H, s), 8.55 (1H, s), 10.78 (1H, s); m/z: ES+ [M+H]+ 467.

Preparation of 4-((6,7-Dimethoxyquinazolin-4-yl)oxy)-3-fluoroaniline

Sodium hydride (60 mg, 2.5 mmol) was added to a mixture of 4-amino-2-fluorophenol (200 mg, 1.6 mmol) and 4-chloro-6,7-dimethoxyquinazoline (424 mg, 1.9 mmol) in DMSO (8 mL) under nitrogen. The resulting mixture was stirred at 80° C. for 1 hour, then concentrated. The crude product was purified by flash silica chromatography, elution gradient 1 to 10% methanol in DCM. Pure fractions were evaporated to dryness to afford the title compound as a black oil (320 mg, 65%). $^1$H NMR (DMSO-d6, 300 MHz) δ 3.99 (6H, d), 5.42 (2H, s), 6.33-6.57 (2H, m), 7.06 (1H, t), 7.40 (1H, s), 7.54 (1H, s), 8.56 (1H, s); m/z: ES+ [M+H]+ 316.

Example 5

2-(4-Isopropyl-1H-1,2,3-triazol-1-yl)-N-(4-((6-methoxy-7-(2-methoxyethoxy) quinazolin-4-yl)oxy) phenyl)acetamide

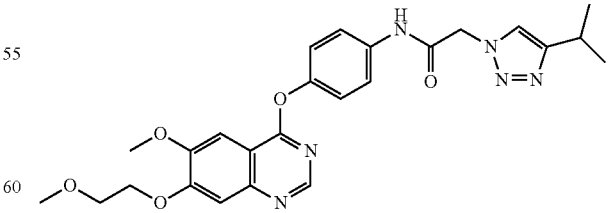

DIPEA (0.26 mL, 1.5 mmol) was added to a solution of 2-(4-isopropyl-1H-1,2,3-triazol-1-yl)acetic acid (0.14 g, 0.4 mmol), 4-((6-methoxy-7-(2-methoxyethoxy)quinazolin-4-yl)oxy)aniline (0.1 g, 0.3 mmol) and HATU (0.19 g, 0.5 mmol) in DMF (2 mL). The solution was stirred at room temperature for 4 hours. The reaction was diluted with ethyl acetate (50 mL) then washed with saturated NaHCO₃ (25 mL) and brine (25 mL). The organic phase was dried, filtered and concentrated under vacuum. The crude product was purified by preparative HPLC. Fractions containing the desired compound were evaporated to dryness to afford the title compound as a white solid (0.065 g, 45%). ¹H NMR (500 MHz, DMSO, 27° C.) δ 1.25 (6H, d), 2.95-3.05 (1H, m), 3.34 (3H, s), 3.73-3.83 (2H, m), 3.97 (3H, s), 4.25-4.36 (2H, m), 5.28 (2H, s), 7.19-7.32 (2H, m), 7.39 (1H, s), 7.55 (1H, s), 7.62-7.73 (2H, m), 7.87 (1H, d), 8.52 (1H, s), 10.56 (1H, s). m/z: ES+ [M+H]+ 493.

Preparation of 4-((6-Methoxy-7-(2-methoxyethoxy)quinazolin-4-yl)oxy)aniline

60% Sodium hydride dispersion (0.04 g, 1 mmol) was added portionwise to DMSO (2 mL) at 22° C. under nitrogen. The resulting slurry was stirred at ambient temperature for 10 minutes. 4-Aminophenol (0.11 g, 1 mmol) was added to the mixture at 22-25° C. under nitrogen. The resulting grey slurry was stirred at ambient temperature for 10 minutes. 4-Chloro-6-methoxy-7-(2-methoxyethoxy)quinazoline (prepared as described in Journal of Medicinal Chemistry, 1999, 42(26), 5369-5389, compound 56, 0.25 g, 0.93 mmol) was added to the mixture at 22-25° C. under nitrogen. The resulting red slurry was stirred at 90° C. for 1 hour then cooled to ambient temperature. Water (20 mL) was added and the reaction was extracted with ethyl acetate (100 mL). The organic phase was separated and washed with brine (20 mL), dried, filtered and concentrated under vacuum to afford the title compound as a brown gum (0.1 g, 32%), which was used without further purification. ¹H NMR (500 MHz, CDCl₃, 27° C.) δ 3.48 (3H, s), 3.77 (2H, s), 3.83-3.92 (2H, m), 4.02 (3H, s), 4.31-4.39 (2H, m), 6.73-6.78 (2H, m), 6.98-7.06 (2H, m), 7.30 (1H, d), 7.54 (1H, s), 8.62 (1H, s). m/z: ES+ [M+H]+ 342.

Example 6

2-(4-Isopropyl-1H-1,2,3-triazol-1-yl)-N-(4-((6-methoxy-7-(2-(pyrrolidin-1-yl)ethoxy)quinazolin-4-yl)oxy)phenyl)acetamide

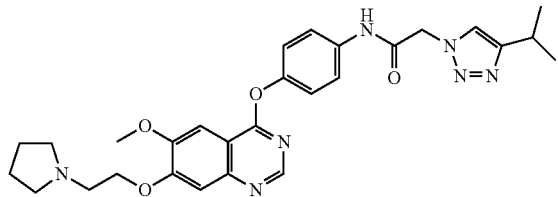 [SMILES: COc1cc2c(Oc3ccc(NC(=O)Cn4cc(C(C)C)nn4)cc3)ncnc2cc1OCCN1CCCC1]

HATU (421 mg, 1.1 mmol) was added to a solution of 2-(4-isopropyl-1H-1,2,3-triazol-1-yl)acetic acid (342 mg, 0.9 mmol), 4-((6-methoxy-7-(2-(pyrrolidin-1-yl)ethoxy)quinazolin-4-yl)oxy)aniline (248 mg, 0.7 mmol) and DIPEA (0.57 mL, 3.3 mmol) in DMF (10 mL). The solution was stirred at ambient temperature for 16 hours. The reaction mixture was partitioned between ethyl acetate (80 mL) and water (80 mL). The aqueous layer was extracted with ethyl acetate (3×80 mL) and the extracts combined with the organic layer. The combined extracts were washed with water (3×80 mL) and saturated brine (80 mL), dried, filtered and concentrated under vacuum. The crude product was purified by flash silica chromatography, elution gradient 3 to 6% (10:1 methanol/conc. NH₃ (aq)) in DCM. Pure fractions were evaporated to dryness and the residue crystallised from acetonitrile to afford the title compound as a white crystalline solid (119 mg, 34%). ¹H NMR (500 MHz, DMSO, 27° C.) δ 1.25 (6H, d), 1.65-1.72 (4H, m), 2.53-2.6 (4H, m), 2.88 (2H, t), 3.00 (1H, hept), 3.96 (3H, s), 4.28 (2H, t), 5.28 (2H, s), 7.28 (2H, d), 7.39 (1H, s), 7.54 (1H, s), 7.67 (2H, d), 7.87 (1H, d), 8.52 (1H, s), 10.55 (1H, s); m/z: ES+ [M+H]+ 532.

Preparation of 4-((6-Methoxy-7-(2-(pyrrolidin-1-yl)ethoxy)quinazolin-4-yl)oxy)aniline 60% Sodium hydride dispersion (0.07 g, 1.8 mmol) was added portionwise to DMSO (4 mL) at 22° C. under nitrogen. The resulting slurry was stirred at ambient temperature for 10 minutes. 4-Aminophenol (0.2 g, 1.8 mmol) was added to the mixture at 22-25° C. under nitrogen and the resulting grey slurry was stirred at ambient temperature for 10 minutes. 4-Chloro-6-methoxy-7-(2-(pyrrolidin-1-yl)ethoxy)quinazoline (prepared as described in U.S. Pat. No. 6,265,411, 2001, example 28, 0.5 g, 1.6 mmol) was added to the mixture at 22-25° C. under nitrogen and the resulting red slurry was stirred at 90° C. for 1 hour. The reaction mixture was cooled to ambient temperature and poured into water (20 mL). The mixture was extracted with ethyl acetate (2×50 mL) and the combined organic phases were washed with brine (20 mL). The organic phase was dried, filtered and concentrated under vacuum to afford the title compound as a beige gum (0.38 g, 62%) which was used without further purification. ¹H NMR (500 MHz, CDCl₃, 27° C.) δ 1.79-1.87 (4H, m), 2.66-2.73 (4H, m), 3.06 (2H, t), 3.77 (2H, s), 4.01 (3H, s), 4.32 (2H, t), 6.72-6.78 (2H, m), 6.97-7.05 (2H, m), 7.27-7.31 (1H, m), 7.54 (1H, s), 8.62 (1H, s); m/z: ES+ [M+H]+ 381.

Example 7

N-(4-((7-(2-(Dimethylamino)ethoxy)-6-methoxyquinazolin-4-yl)oxy)phenyl)-2-(4-isopropyl-1H-1,2,3-triazol-1-yl)acetamide

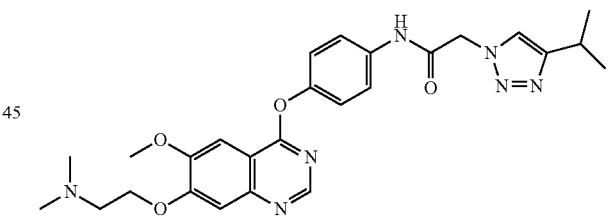

To a suspension of potassium carbonate (120 mg, 0.9 mmol) and N-(4-((7-hydroxy-6-methoxyquinazolin-4-yl)oxy)phenyl)-2-(4-isopropyl-1H-1,2,3-triazol-1-yl)acetamide (126 mg, 0.3 mmol) in DMF (4 ml) was added 2-(dimethylamino)ethyl methanesulfonate (49 mg, 0.3 mmol) and the reaction was heated at 90° C. for 18 hours. Additional 2-(dimethylamino)ethyl methanesulfonate (97 mg, 0.6 mmol) was added and the reaction was stirred at 90° C. for a further 16 hours. The reaction mixture was diluted with ethyl acetate (50 mL) and washed with saturated NaHCO₃ solution (20 mL) and brine (20 mL). The organic layer was dried, filtered and concentrated under vacuum. The crude product was purified by preparative HPLC. Fractions containing the desired compound were evaporated to dryness to afford the title compound as a white solid (21 mg, 14%). ¹H NMR (500 MHz, CDCl₃, 27° C.) δ 1.35 (6H, d), 2.39 (6H, s), 2.90 (2H, t), 3.10-3.20 (1H, m), 4.03 (3H, s), 4.29 (2H, t), 5.18 (2H, s), 7.19-7.24 (2H, m), 7.31 (1H, s), 7.49 (1H, d), 7.52 (1H, s), 7.58-7.63 (2H, m), 8.28 (1H, s), 8.58 (1H, s). m/z: ES+ [M+H]+ 506.

The intermediates used in Example 7 were prepared as follows:

Preparation of 2-(Dimethylamino)ethyl methanesulfonate

To a solution of 2-(dimethylamino)ethan-1-ol (0.03 mL, 0.3 mmol) in DCM (2 mL) was added triethylamine (0.13 mL, 1 mmol) and methanesulfonyl chloride (0.03 mL, 0.4 mmol) at 0° C. The reaction was stirred at ambient temperature for 3 hours. The reaction mixture was evaporated to dryness to afford crude product which was progressed without further purification.

Preparation of N-(4-((7-Hydroxy-6-methoxyquinazolin-4-yl)oxy)phenyl)-2-(4-isopropyl-1H-1,2,3-triazol-1-yl)acetamide 10% Palladium on activated charcoal (0.05 g, 0.5 mmol) was added to a solution of N-(4-((7-(benzyloxy)-6-methoxyquinazolin-4-yl)oxy)phenyl)-2-(4-isopropyl-1H-1,2,3-triazol-1-yl)acetamide (0.25 g, 0.5 mmol) in ethanol (20 mL) and NMP (2 mL) under nitrogen. The mixture was then stirred at ambient temperature under an atmosphere of hydrogen for 16 hours. The reaction was filtered through Celite; the Celite was washed with methanol (60 mL). The combined filtrates were concentrated under vacuum and the crude product was purified by preparative HPLC. Fractions containing the desired compound were combined and the solution was adjusted to pH7-8. The product was extracted with ethyl acetate (2×100 mL). The combined extractions were washed with brine (40 mL), dried, filtered and evaporated to dryness to afford the title compound as a white solid (0.13 g, 61%). $^1$H NMR (500 MHz, DMSO, 27° C.) δ 1.25 (6H, d), 2.94-3.05 (1H, m), 3.97 (3H, s), 5.28 (2H, s), 7.21 (1H, s), 7.23-7.32 (2H, m), 7.54 (1H, s), 7.63-7.72 (2H, m), 7.87 (1H, d), 8.45 (1H, s), 10.55 (1H, s), 10.72 (1H, s); m/z: ES+ [M+H]+ 435.

Preparation of N-(4-((7-(Benzyloxy)-6-methoxyquinazolin-4-yl)oxy)phenyl)-2-(4-isopropyl-1H-1,2,3-triazol-1-yl)acetamide DIPEA (0.58 mL, 3.4 mmol) was added to a solution of 2-(4-isopropyl-1H-1,2,3-triazol-1-yl)acetic acid (0.38 g, 1 mmol), 4-((7-(benzyloxy)-6-methoxyquinazolin-4-yl)oxy)aniline (0.25 g, 0.7 mmol) and HATU (0.43 g, 1.1 mmol) in DMF (5 mL). This solution was stirred at room temperature for 2 hours. The reaction was diluted with ethyl acetate (150 mL) then washed with saturated NaHCO$_3$ (50 mL) and brine (50 mL). The organic phase was dried, filtered and concentrated under vacuum. The crude product was purified by flash silica chromatography, elution gradient 0 to 4% methanol in DCM. Pure fractions were evaporated to dryness to afford the title compound as a beige solid (0.25 g, 72%). $^1$H NMR (500 MHz, DMSO, 27° C.) δ 1.25 (6H, d), 2.87-3.05 (1H, m), 3.97 (3H, s), 5.28 (2H, s), 5.34 (2H, s), 7.04-7.3 (2H, m), 7.31-7.4 (1H, m), 7.41-7.47 (2H, m), 7.45-7.55 (3H, m), 7.57 (1H, s), 7.63-7.73 (2H, m), 7.87 (1H, d), 8.52 (1H, s), 10.55 (1H, s); m/z: ES+ [M+H]+ 525.

Preparation of 4-((7-(Benzyloxy)-6-methoxyquinazolin-4-yl)oxy)aniline

60% Sodium hydride dispersion (0.12 g, 3.1 mmol) was added portionwise to DMSO (6 mL) at 22° C. under nitrogen. The resulting slurry was stirred at ambient temperature for 10 minutes. 4-Aminophenol (0.34 g, 3.1 mmol) was added to the mixture at 22-25° C. under nitrogen. The resulting grey slurry was stirred at ambient temperature for 10 minutes. 7-(Benzyloxy)-4-chloro-6-methoxyquinazoline (prepared as described in Journal of Medicinal Chemistry, 1999, 42(26), 5369-5389, compound 41, 0.85 g, 2.8 mmol) was added to the mixture at 22-25° C. under nitrogen. The resulting red slurry was stirred at 90° C. for 1 hour. The reaction mixture was cooled to ambient temperature and poured into stirred water (50 mL). The precipitate was collected by filtration, washed with water (2×20 mL) and air dried to afford the title compound (0.95 g, 91%) as a beige solid, which was used without further purification. $^1$H NMR (500 MHz, DMSO, 27° C.) δ 3.97 (3H, s), 5.06 (2H, s), 5.34 (2H, s), 6.55-6.65 (2H, m), 6.87-6.96 (2H, m), 7.34-7.40 (1H, m), 7.40-7.47 (3H, m), 7.48-7.56 (3H, m), 8.50 (1H, s); m/z: ES+[M+H]+ 374.

Example 8

N-(4-((7-(2-Hydroxyethoxy)-6-methoxyquinazolin-4-yl)oxy)phenyl)-2-(4-isopropyl-1H-1,2,3-triazol-1-yl)acetamide

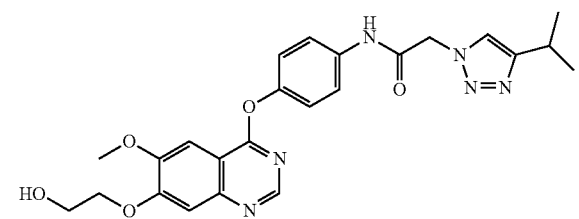 [SMILES: COc1cc2c(Oc3ccc(NC(=O)Cn4cc(C(C)C)nn4)cc3)ncnc2cc1OCCO]

10% Palladium on activated charcoal (39 mg, 0.037 mmol) was added to a solution of N-(4-((7-(2-(benzyloxy)ethoxy)-6-methoxyquinazolin-4-yl)oxy)phenyl)-2-(4-isopropyl-1H-1,2,3-triazol-1-yl)acetamide (0.21 g, 0.37 mmol) in ethanol (20 mL) and NMP (2 mL) under a stream of nitrogen. The mixture was then stirred at ambient temperature under an atmosphere of hydrogen for 16 hours. Additional 10% Palladium on activated charcoal (39 mg, 0.037 mmol) was added and the reaction was stirred at ambient temperature for a further 24 hours. The reaction was filtered through Celite; the Celite was washed with methanol (50 mL). The combined filtrates were concentrated under vacuum and the crude product was purified by preparative HPLC. Fractions containing the desired product were combined and concentrated under vacuum. The residue was triturated with ether to afford the title compound as a white solid (15 mg, 8%). $^1$H NMR (500 MHz, DMSO, 27° C.) δ 1.25 (6H, d), 2.94-3.05 (1H, m), 3.81 (2H, q), 3.97 (3H, s), 4.15-4.25 (2H, m), 4.96 (1H, t), 5.28 (2H, s), 7.23-7.33 (2H, m), 7.38 (1H, s), 7.55 (1H, s), 7.63-7.70 (2H, m), 7.87 (1H, d), 8.52 (1H, s), 10.55 (1H, s); m/z: ES+ [M+H]+ 479.

Preparation of N-(4-((7-(2-(Benzyloxy)ethoxy)-6-methoxyquinazolin-4-yl)oxy)phenyl)-2-(4-isopropyl-1H-1,2,3-triazol-1-yl)acetamide To a solution of 2-(benzyloxy)ethan-1-ol (0.19 mL, 1.3 mmol) in DCM (5 mL) was added triethylamine (0.55 mL, 3.9 mmol) and methanesulfonyl chloride (0.12 mL, 1.6 mmol) at 0° C. The reaction was stirred at ambient temperature for 3 hours, then evaporated to dryness. The residue was dissolved in DMF (3 mL) and 1.7 mL of this solution was added to a suspension of potassium carbonate (153 mg, 1.1 mmol) and N-(4-((7-hydroxy-6-methoxyquinazolin-4-yl)oxy)phenyl)-2-(4-isopropyl-1H-1,2,3-triazol-1-yl)acetamide (160 mg, 0.4 mmol) in DMF (2.3 mL) and the reaction was heated at 90° C. for 6 hours. The reaction mixture was diluted with ethyl acetate (50 mL) and washed with water (20 mL) and brine (20 mL). The organic layer was dried, filtered and concentrated under vacuum to afford the title compound (0.21 g, 100%) as a yellow liquid, which was used without further purification. m/z: ES+ [M+H]+ 569.

Example 9

2-(4-Isopropyl-1H-1,2,3-triazol-1-yl)-N-(4-((6-methoxy-7-((tetrahydro-2H-pyran-4-yl)oxy)quinazolin-4-yl)oxy)phenyl)acetamide

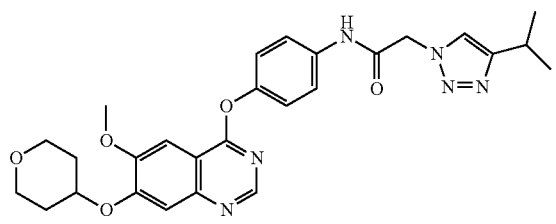 [SMILES: COc1cc2c(Oc3ccc(NC(=O)Cn4cc(C(C)C)nn4)cc3)ncnc2cc1OC1CCOCC1]

Cesium carbonate (450 mg, 1.4 mmol) was added to a solution of N-(4-((7-hydroxy-6-methoxyquinazolin-4-yl)oxy)phenyl)-2-(4-isopropyl-1H-1,2,3-triazol-1-yl)acetamide (200 mg, 0.5 mmol) and 4-bromotetrahydro-2H-pyran (456 mg, 2.8 mmol) in DMF (3 mL) under nitrogen. The resulting mixture was stirred at 100° C. for 3 hours. The crude product was purified by preparative HPLC. Fractions containing the desired product were combined and concentrated under vacuum to afford the title compound as a white solid (124 mg, 52%). $^1$H NMR (400 MHz, DMSO-d6) δ 1.26 (6H, d), 1.61-1.75 (2H, m), 2.09 (2H, d), 2.95-3.07 (1H, m), 3.57-3.59 (2H, m), 3.86-3.95 (2H, m), 3.98 (3H, s), 4.94-4.96 (1H, m), 5.30 (2H, s), 7.25-7.33 (2H, m), 7.55 (2H, d), 7.64-7.73 (2H, m), 7.90 (1H, d), 8.54 (1H, s), 10.59 (1H, s); m/z: ES+ [M+H]+ 519.

Example 10

2-(4-Isopropyl-1H-1,2,3-triazol-1-yl)-N-(4-((6-methoxy-7-(oxetan-3-yloxy)quinazolin-4-yl)oxy)phenyl)acetamide

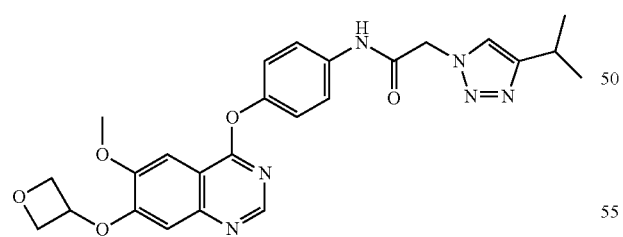

Cesium carbonate (450 mg, 1.4 mmol) was added to a solution of N-(4-((7-hydroxy-6-methoxyquinazolin-4-yl)oxy)phenyl)-2-(4-isopropyl-1H-1,2,3-triazol-1-yl)acetamide (200 mg, 0.5 mmol) and 3-bromooxetane (315 mg, 2.3 mmol) in DMF (3 mL) under nitrogen. The resulting mixture was stirred at 100° C. for 4 hours. The crude product was purified by preparative HPLC. Fractions containing the desired product were combined and concentrated under vacuum to afford the title compound as a white solid (56 mg, 25%). 1H NMR (400 MHz, DMSO-d6) δ 1.26 (6H, d), 3.01 (1H, p), 4.01 (3H, s), 4.60-4.68 (2H, m), 5.05 (2H, t), 5.29 (2H, s), 5.56-5.58 (1H, m), 7.03 (1H, s), 7.29 (2H, d), 7.62 (1H, s), 7.69 (2H, d), 7.89 (1H, s), 8.54 (1H, s), 10.58 (1H, s); m/z: ES+ [M+H]+ 491.

Example 11

N-[4-(7-Isopropoxy-6-methoxy-quinazolin-4-yl)oxyphenyl]-2-(4-isopropyl-1H-1,2,3-triazol-1-yl)acetamide

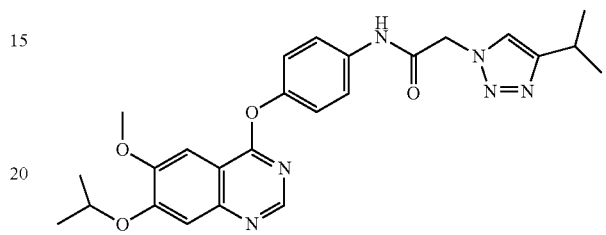

Cesium carbonate (675 mg, 2.1 mmol) was added to a solution of N-(4-((7-hydroxy-6-methoxyquinazolin-4-yl)oxy)phenyl)-2-(4-isopropyl-1H-1,2,3-triazol-1-yl)acetamide (300 mg, 0.7 mmol) and 2-bromopropane (425 mg, 3.5 mmol) in DMF (5 mL) under nitrogen. The resulting mixture was stirred at 60° C. for 3 hours. The crude product was purified by preparative HPLC. Fractions containing the desired product were combined and concentrated under vacuum to afford the title compound as a white solid (68 mg, 21%). $^1$H NMR (400 MHz, DMSO-d6) δ 1.26 (6H, t), 1.33-1.42 (6H, m), 2.96-3.06 (1H, m), 3.93-3.99 (3H, m), 4.94 (1H, d), 5.26-5.33 (2H, m), 7.29 (2H, d), 7.35-7.41 (1H, m), 7.55 (1H, t), 7.68 (2H, t), 7.89 (1H, t), 8.52 (1H, t), 10.58 (1H, d); m/z: ES+ [M+H]+ 477.

Example 12 and Example 13

(R)-2-(4-Isopropyl-1H-1,2,3-triazol-1-yl)-N-(4-((6-methoxy-7-((tetrahydrofuran-3-yl)oxy)quinazolin-4-yl)oxy)phenyl)acetamide and (S)-2-(4-isopropyl-1H-1,2,3-triazol-1-yl)-N-(4-((6-methoxy-7-((tetrahydrofuran-3-yl)oxy)quinazolin-4-yl)oxy)phenyl)acetamide

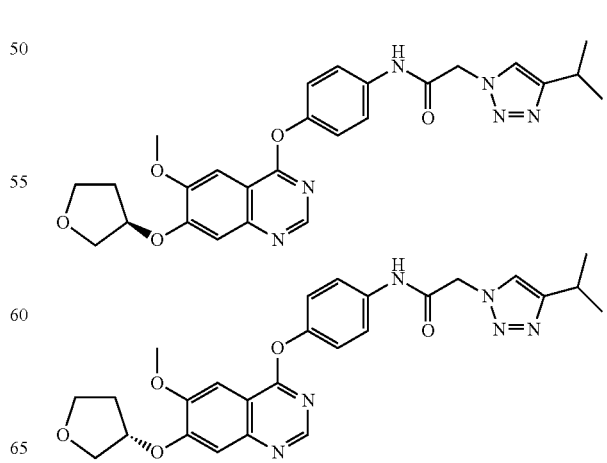

Cesium carbonate (0.9 g, 2.8 mmol) was added to a solution of N-(4-((7-hydroxy-6-methoxyquinazolin-4-yl)oxy)phenyl)-2-(4-isopropyl-1H-1,2,3-triazol-1-yl)acetamide (0.4 g, 0.9 mmol) and 3-bromotetrahydrofuran (0.7 g, 4.6 mmol) in DMF (3 mL) under nitrogen. The resulting mixture was stirred at 100° C. for 3 hours. The crude product was purified by preparative HPLC. Fractions containing the desired product were combined and concentrated under vacuum to afford racemic title compound as a white solid (180 mg, 39%). This was purified by preparative SFC-HPLC. The first eluting fractions containing the desired compound were evaporated to dryness to afford one enantiomer of 2-(4-isopropyl-1H-1,2,3-triazol-1-yl)-N-(4-((6-methoxy-7-((tetrahydrofuran-3-yl)oxy)quinazolin-4-yl)oxy)phenyl)acetamide as a white solid (69 mg, 38%, 100% e.e.). $^1$H NMR (400 MHz, DMSO-d6) δ 1.26 (6H, d), 2.06-2.08 (1H, m), 2.38-2.40 (1H, m), 3.01-3.03 (1H, m), 3.74-4.03 (7H, m), 5.31 (3H, d), 7.26-7.34 (2H, m), 7.37 (1H, s), 7.58 (1H, s), 7.64-7.76 (2H, m), 7.90 (1H, d), 8.55 (1H, s), 10.60 (1H, s); m/z: ES+ [M+H]+ 505. This was followed by the other enantiomer of 2-(4-isopropyl-1H-1,2,3-triazol-1-yl)-N-(4-((6-methoxy-7-((tetrahydrofuran-3-yl)oxy)quinazolin-4-yl)oxy)phenyl)acetamide (67 mg, 37%, 100% e.e.) as a white solid. $^1$H NMR (400 MHz, DMSO-d6) δ 1.26 (6H, d), 2.06-2.08 (1H, m), 2.38-2.40 (1H, m), 3.01-3.03 (1H, m), 3.74-4.03 (7H, m), 5.28-5.36 (3H, m), 7.25-7.34 (2H, m), 7.37 (1H, s), 7.57 (1H, s), 7.64-7.73 (2H, m), 7.90 (1H, d), 8.55 (1H, s), 10.57-10.63 (1H, m); m/z: ES+ [M+H]+ 505.

The invention claimed is:

1. A compound of Formula (I):

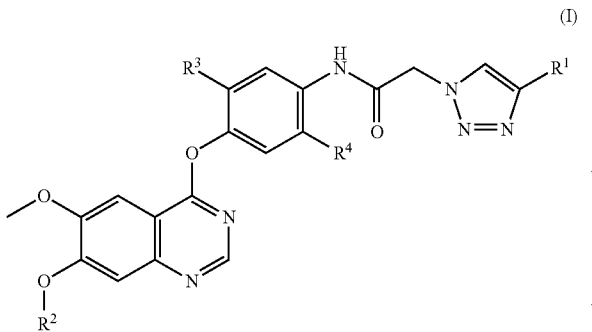

(I)

or a pharmaceutically acceptable salt thereof, wherein:
$R^1$ is a $C_{2-3}$ alkyl or a cyclopropyl group;
$R^2$ is a $C_{1-3}$ alkyl, optionally substituted with a group selected from hydroxyl, $C_{1-3}$ alkoxyl and —$NR^5R^6$, where $R^5$ and $R^6$ are each independently hydrogen or methyl or $R^5$ and $R^6$ together with the nitrogen to which they are attached form a 5 membered heterocyclyl ring; or a 4 to 6 membered heterocyclyl containing one oxygen atom;
$R^3$ is hydrogen or fluoro; and
$R^4$ is hydrogen or methoxy.

2. The compound of Formula (I), or a pharmaceutically acceptable salt thereof as claimed in claim 1, wherein $R^1$ is isopropyl.

3. The compound of Formula (I), or a pharmaceutically acceptable salt thereof as claimed in claim 1, wherein $R^2$ is methyl.

4. The compound of Formula (I), or a pharmaceutically acceptable salt thereof as claimed in claim 1, wherein $R^3$ and $R^4$ are both hydrogen.

5. The compound of Formula (I), or a pharmaceutically acceptable salt thereof as claimed in claim 1, wherein the compound of Formula (I) is selected from the group consisting of:
N-(4-((6,7-Dimethoxyquinazolin-4-yl)oxy)phenyl)-2-(4-isopropyl-1H-1,2,3-triazol-1-yl)acetamide;
2-(4-Cyclopropyl-1H-1,2,3-triazol-1-yl)-N-(4-((6,7-dimethoxyquinazolin-4-yl)oxy)phenyl)acetamide;
N-(4-((6,7-Dimethoxyquinazolin-4-yl)oxy)-2-methoxyphenyl)-2-(4-isopropyl-1H-1,2,3-triazol-1-yl)acetamide;
N-(4-((6,7-Dimethoxyquinazolin-4-yl)oxy)-3-fluorophenyl)-2-(4-isopropyl-1H-1,2,3-triazol-1-yl)acetamide;
2-(4-Isopropyl-1H-1,2,3-triazol-1-yl)-N-(4-((6-methoxy-7-(2-methoxyethoxy)quinazolin-4-yl)oxy)phenyl)acetamide;
2-(4-Isopropyl-1H-1,2,3-triazol-1-yl)-N-(4-((6-methoxy-7-(2-(pyrrolidin-1-yl)ethoxy)quinazolin-4-yl)oxy)phenyl)acetamide
N-(4-((7-(2-(Dimethylamino)ethoxy)-6-methoxyquinazolin-4-yl)oxy)phenyl)-2-(4-isopropyl-1H-1,2,3-triazol-1-yl)acetamide;
N-(4-(7-(2-Hydroxyethoxy)-6-methoxyquinazolin-4-yl)oxy)phenyl)-2-(4-isopropyl-1H-1,2,3-triazol-1-yl)acetamide;
2-(4-Isopropyl-1H-1,2,3-triazol-1-yl)-N-(4-((6-methoxy-7-((tetrahydro-2H-pyran-4-yl)oxy)quinazolin-4-yl)oxy)phenyl)acetamide;
2-(4-Isopropyl-1H-1,2,3-triazol-1-yl)-N-(4-((6-methoxy-7-(oxetan-3-yloxy)quinazolin-4-yl)oxy)phenyl)acetamide;
N-[4-(7-Isopropoxy-6-methoxy-quinazolin-4-yl)oxyphenyl]-2-(4-isopropyl-1H-1,2,3-triazol-1-yl)acetamide;
(R)-2-(4-Isopropyl-1H-1,2,3-triazol-1-yl)-N-(4-((6-methoxy-7-((tetrahydrofuran-3-yl)oxy)quinazolin-4-yl)oxy)phenyl)acetamide; and
(S)-2-(4-Isopropyl-1H-1,2,3-triazol-1-yl)-N-(4-((6-methoxy-7-((tetrahydrofuran-3-yl)oxy)quinazolin-4-yl)oxy)phenyl)acetamide.

6. The compound of Formula (I), or a pharmaceutically acceptable salt thereof as claimed in claim 1, wherein the compound is N-(4-(6,7-Dimethoxyquinazolin-4-yl)oxy)phenyl)-2-(4-isopropyl-1H-1,2,3-triazol-1-yl)acetamide.

7. A compound of Formula (I), as claimed in claim 1, wherein the compound is in the free base form.

8. A compound of Formula (I), as claimed in claim 6 in crystalline form with an XRPD substantially as shown in FIG. 1 and measured using CuKα radiation.

9. A compound of Formula (I), as claimed in claim 6 in crystalline form with an XRPD substantially as shown in FIG. 2 and measured using CuKα radiation.

10. A pharmaceutical composition which comprises a compound of Formula (I), or a pharmaceutically acceptable salt thereof as claimed in claim 1, and at least one pharmaceutically acceptable diluent or carrier.

* * * * *

UNITED STATES PATENT AND TRADEMARK OFFICE
CERTIFICATE OF CORRECTION

PATENT NO. : 11,053,223 B2  
APPLICATION NO. : 16/608212  
DATED : July 6, 2021  
INVENTOR(S) : Tudor Grecu et al.

Page 1 of 1

It is certified that error appears in the above-identified patent and that said Letters Patent is hereby corrected as shown below:

In the Claims

Column 34, Line 24, Claim 5 "acetamide" should be -- acetamide; --.

Column 34, Line 28, Claim 5 "N-(4-(7-(2-" should be -- N-(4-((7-(2- --.

Column 34, Line 47, Claim 5 "N-(4-(6,7-" should be -- N-(4-((6,7- --.

Signed and Sealed this  
Fifteenth Day of February, 2022

Drew Hirshfeld  
*Performing the Functions and Duties of the*  
*Under Secretary of Commerce for Intellectual Property and*  
*Director of the United States Patent and Trademark Office*